US012616548B2

(12) United States Patent　　　　　(10) Patent No.:　US 12,616,548 B2

Howe　　　　　(45) **Date of Patent:　*May 5, 2026**

(54) SYSTEMS AND METHODS FOR SURGICAL FIELD ITEM DETECTION

(71) Applicant: Magvation, LLC, Las Vegas, NV (US)

(72) Inventor: Jason Howe, Fallbrook, CA (US)

(73) Assignee: Magvation, LLC, Las Vegas, NV (US)

( * ) Notice: Subject to any disclaimer, the term of this patent is extended or adjusted under 35 U.S.C. 154(b) by 61 days.

This patent is subject to a terminal disclaimer.

(21) Appl. No.: 18/627,868

(22) Filed: Apr. 5, 2024

(65) Prior Publication Data

US 2024/0268916 A1　　Aug. 15, 2024

Related U.S. Application Data

(63) Continuation of application No. 17/829,471, filed on Jun. 1, 2022, now Pat. No. 12,011,320.

(60) Provisional application No. 63/195,924, filed on Jun. 2, 2021.

(51) Int. Cl.
| | |
|---|---|
| *A61B 90/00* | (2016.01) |
| *A61B 50/20* | (2016.01) |
| *A61B 50/36* | (2016.01) |
| *G06V 20/60* | (2022.01) |

(52) U.S. Cl.
CPC .............. *A61B 90/08* (2016.02); *A61B 50/20* (2016.02); *A61B 50/362* (2016.02); *A61B 90/37* (2016.02); *A61B 2050/21* (2016.02); *A61B 2090/0805* (2016.02); *G06V 20/60* (2022.01)

(58) Field of Classification Search
CPC ....... A61B 90/08; A61B 50/20; A61B 50/362;

A61B 90/37; A61B 2050/21; A61B 2090/0805; A61B 2090/0804; A61B 90/06; A61B 2017/00119; A61B 90/361; A61B 90/90; A61B 90/98; A61B 2090/065; A61B 2017/00221; A61B 17/06161; G06V 20/60; G06V 10/82; G06V 20/52; G06V 2201/034; G06N 3/0464; G16H 40/20

See application file for complete search history.

(56) References Cited

U.S. PATENT DOCUMENTS

| | | | |
|---|---|---|---|
| 5,240,108 | A | 8/1993 | Tonna |
| 5,482,207 | A | 1/1996 | Nelson et al. |
| 8,875,881 | B2 | 11/2014 | Smudde et al. |
| 2002/0049650 | A1 | 4/2002 | Reff |
| 2006/0218002 | A1 | 9/2006 | Mallett et al. |
| 2009/0317002 | A1 | 12/2009 | Dein |
| 2014/0374294 | A1 | 12/2014 | Joyce |
| 2018/0338801 | A1 | 11/2018 | Barnett et al. |

(Continued)

OTHER PUBLICATIONS

Patent Cooperation Treaty, PCT/US2022/031706, International Search Report and Written Opinion of the International Searching Authority, dated Sep. 2, 2022.

*Primary Examiner* — Seung H Lee

(74) *Attorney, Agent, or Firm* — Jones Day

(57) ABSTRACT

Systems and methods are provided for a surgical needle counting device for an operating room. An example system includes a collecting enclosure and a counting apparatus having a sensor configured for determining when a needle is dropped into the collecting enclosure. The counting apparatus is configured to maintain a count of needles introduced into a surgical field associated with the operating room and a count of needles accounted for in the counting apparatus.

24 Claims, 22 Drawing Sheets

(56) References Cited

U.S. PATENT DOCUMENTS

| | | |
|---|---|---|
| 2020/0013191 A1 | 1/2020 | Berning |
| 2022/0104903 A1 | 4/2022 | Koclanes et al. |

Charging pads for 3 Internal
Electronic Sensory Enclosures (3)

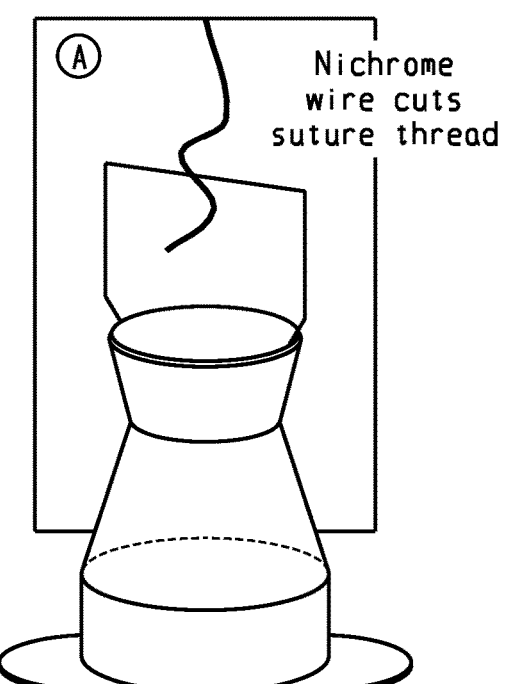
Nichrome
wire cuts
suture thread
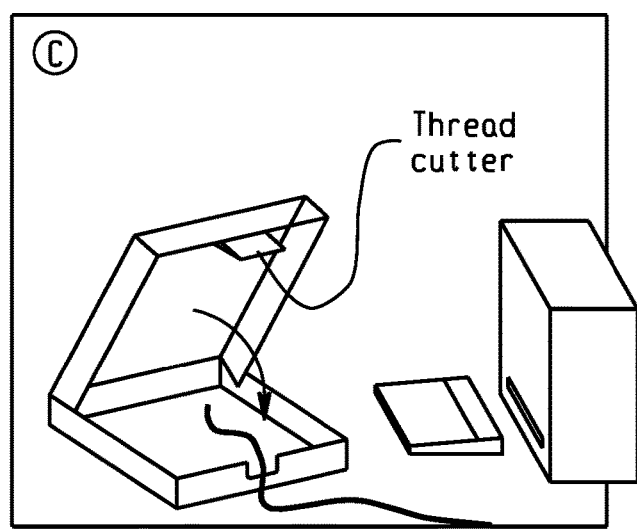
Thread
cutter
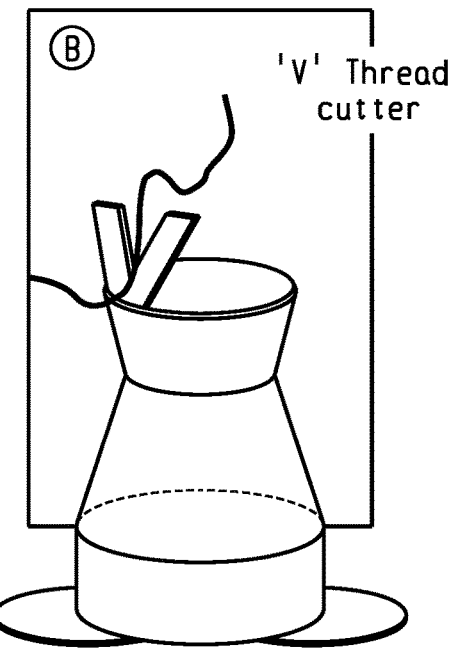
'V' Thread
cutter
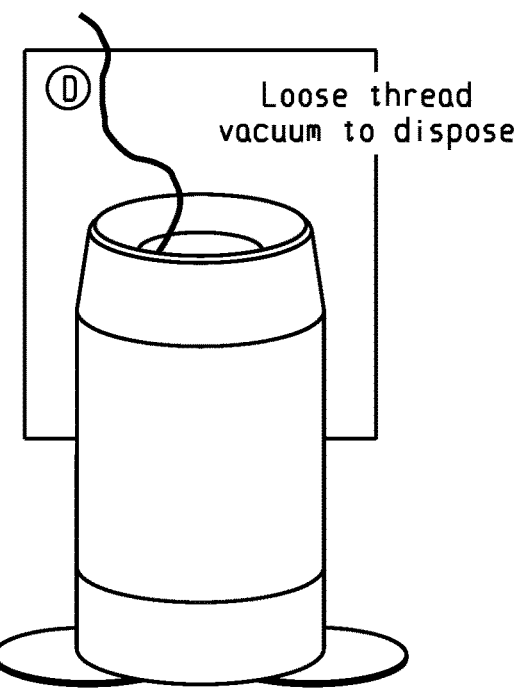
Loose thread
vacuum to dispose
*Fig. 12*

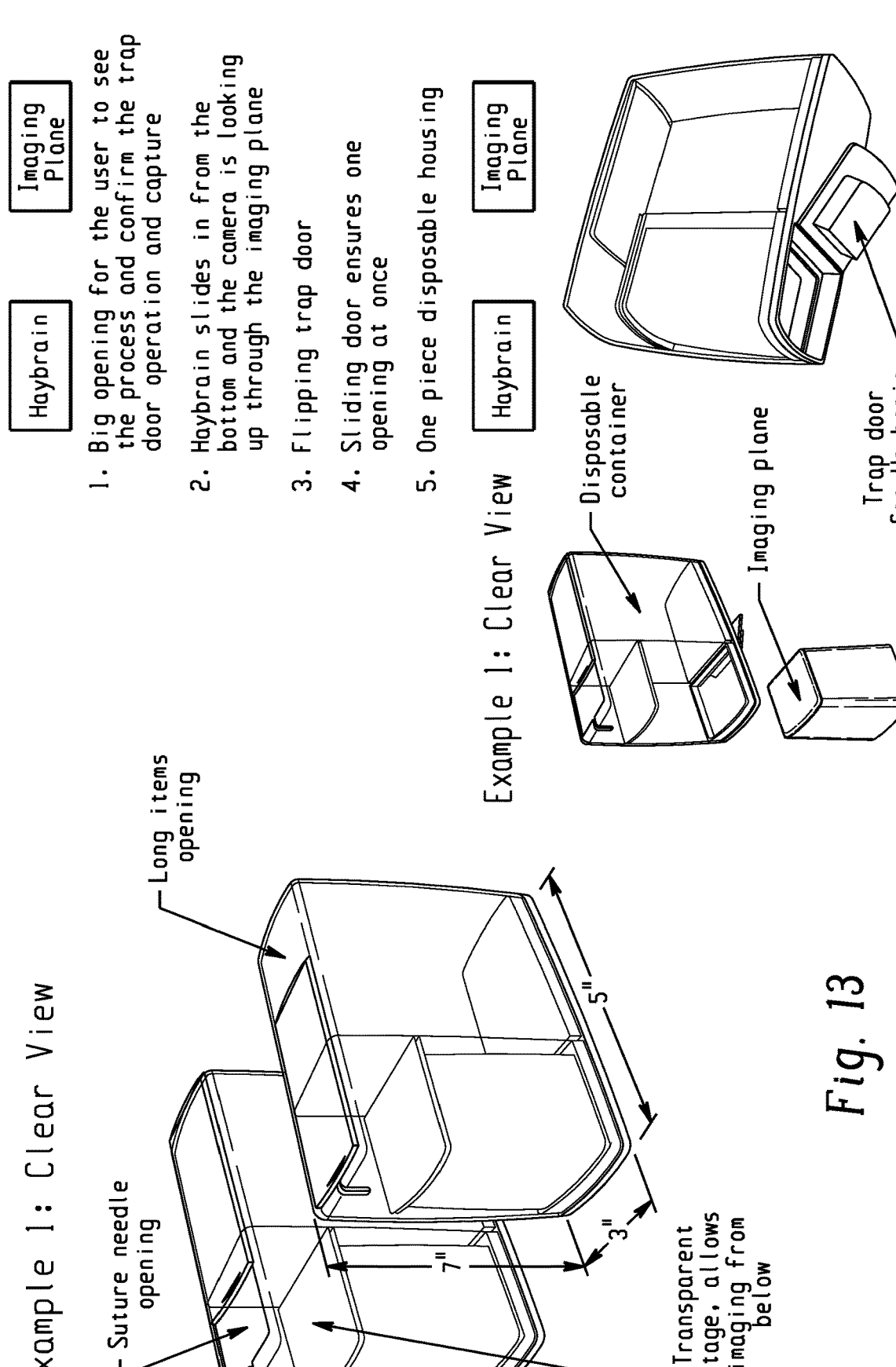

Imaging Plane

Haybrain

1. Big opening for the user to see the process and confirm the trap door operation and capture 2. Haybrain slides in from the bottom and the camera is looking up through the imaging plane 3. Flipping trap door 4. Sliding door ensures one opening at once 5. One piece disposable housing Imaging Plane Haybrain Example 1: Clear View Disposable container Imaging plane Trap door for Haybrain Example 1: Clear View Long items opening Suture needle opening Transparent stage, allows imaging from below

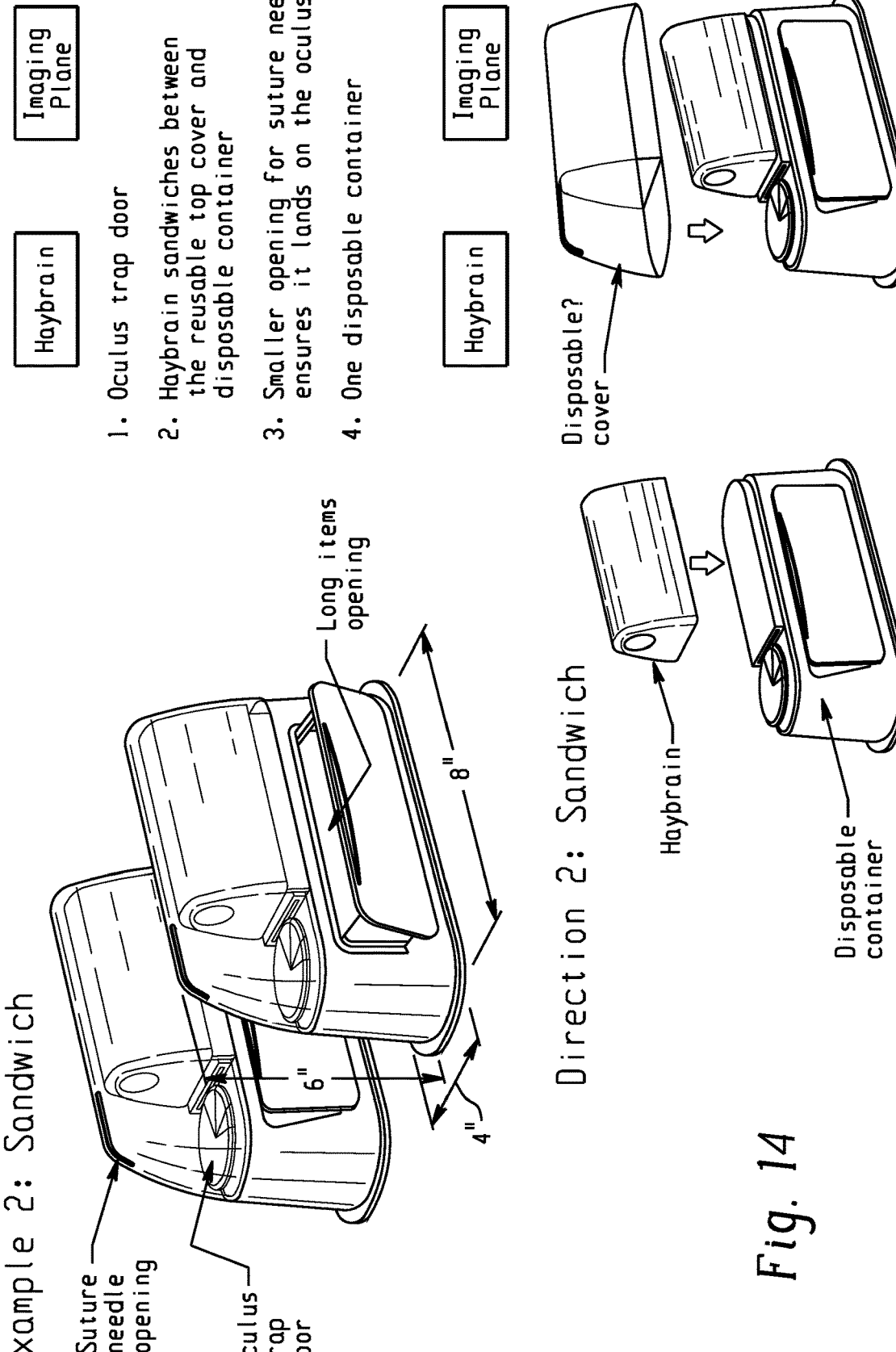

Example 2: Sandwich

| Imaging Plane |  | Haybrain |

1. Oculus trap door
2. Haybrain sandwiches between the reusable top cover and disposable container
3. Smaller opening for suture needle ensures it lands on the oculus
4. One disposable container Suture needle opening Oculus trap door Long items opening

8"

6"

4"

Disposable? cover

| Imaging Plane |  | Haybrain |

Direction 2: Sandwich

Haybrain

Disposable container

*Fig. 14*

Imaging Plane

Haybrain

1. Round space saving design

2. Rotate to switch between modes

3. Rotating trap door

4. Quick and easy drop in assembly

5. One disposable container

Long items opening

Ø 4"

7"

Example 3: Rotate

Suture needle opening

Imaging Plane

Haybrain

1. Transformable stacking design

2. Haybrain and battery seals inside suture needle disposable container

3. Sliding trap door

4. More flexible setup for tabletop and pole mounted operation

5. Two disposable container

Example 4: Modular

Haybrain camera

Suture needle opening

Long items opening

Long items opening

7"

7"

6"

Imaging Plane

Haybrain

Example 4: Modular

Battery

Haybrain

Seal door

*Fig. 18*

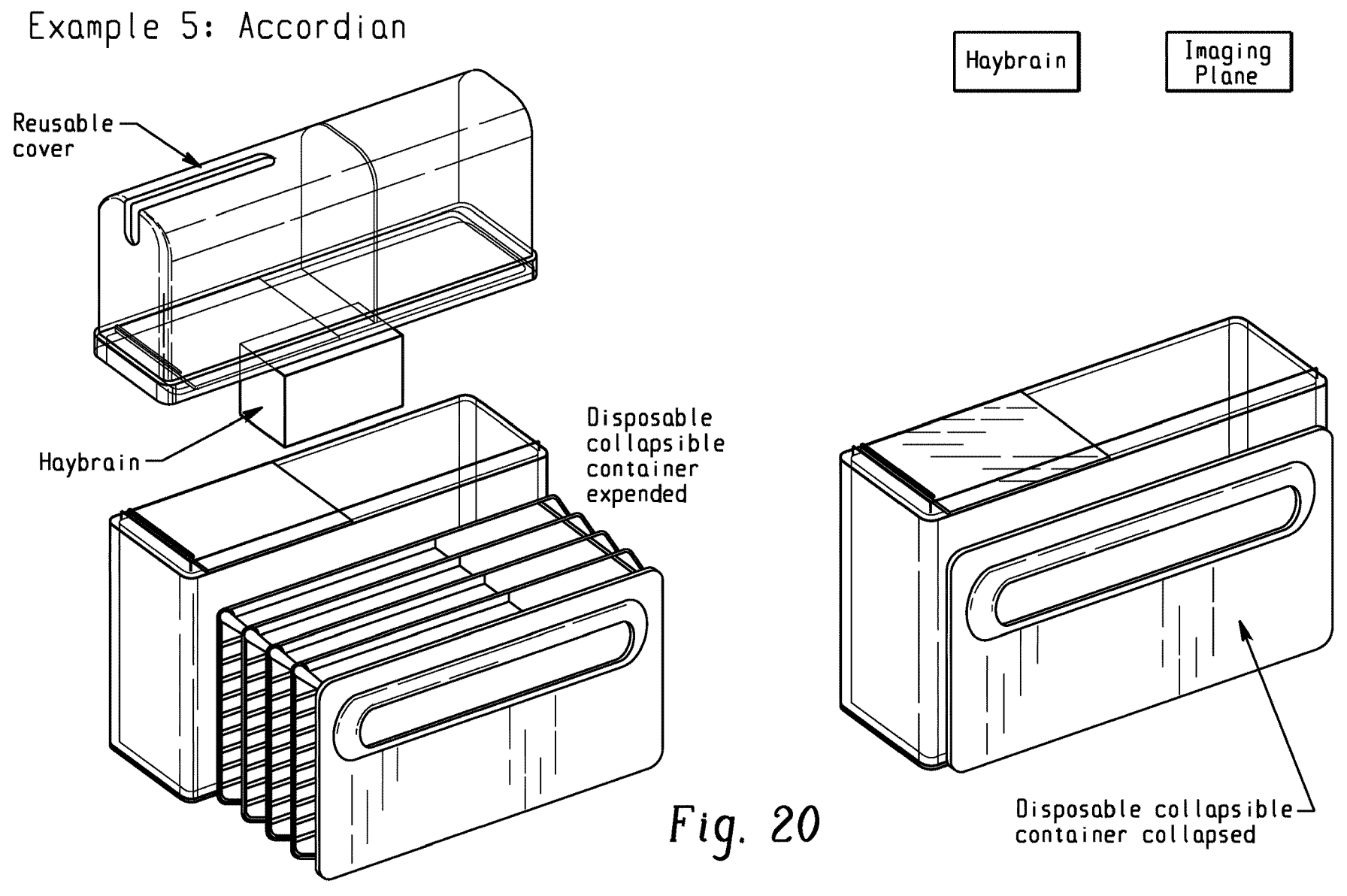

Imaging Plane

Haybrain

Disposable collapsible container collapsed

Disposable collapsible container expended

Example 5: Accordian

Reusable cover

Haybrain

Fig. 20

SYSTEMS AND METHODS FOR SURGICAL FIELD ITEM DETECTION

CROSS-REFERENCE TO RELATED APPLICATIONS

This application is a continuation application of U.S. patent application Ser. No. 17/829,471, filed Jun. 1, 2022, which claims priority to U.S. Provisional Application No. 63/195,924 filed Jun. 2, 2021, both of which are incorporated herein by reference in their entireties.

FIELD

Systems and methods herein relates to a medical counting device and software, suitable for the counting of the number of needles used in statistical operation on a sterile field on a patient in an operating room.

BACKGROUND

Accidental retention of foreign bodies, or Retained Surgical Items (RSI), occurs in approximately 1 of every 1000-1500 operations. Early identification and immediate remediation of such events are paramount to ensure patient safety and address the public's increased awareness of medical error prevention and avoidance. Although a large share of attention is directed toward retained surgical sponges and retained surgical instruments, retained suture-needles and suture-needlesticks are substantive problems that result in injury, morbidity, medicolegal impairments, and even mortality. The National Quality Foundation estimated in 2017, that there were 51 million operations/procedures performed at non-federal hospitals in the US, and in 2019 there were 67 million surgical outpatient procedures performed in ambulatory surgical centers. By a conservative estimate, suture-needle miscounts occur in 4% of operations, suture-needlesticks in 0.5%, and suture-needle retention in 0.06%. Assuming an even more conservative estimate that only 50% of the 134,000,000 operations/procedures utilize suture-needles, there are roughly 2,780,000 needle miscount incidents, 335,000 needlestick incidents, and 40,000 needle retention incidents per year, all with potentially tragic patient outcomes and potentially material financial consequences.

SUMMARY

Systems and methods are provided for a surgical needle counting device for an operating room. An example system includes a collecting enclosure and a counting apparatus having a sensor configured for determining when a needle is dropped into the collecting enclosure. The counting apparatus is configured to maintain a count of needles introduced into a surgical field associated with the operating room and a count of needles accounted for in the counting apparatus.

As another example, a method of detecting a surgical needle in an operating room includes maintaining a count of needles introduced into a surgical field associated with the operating room. A needle is received in a collecting enclosure. A sensor is used to detect the presence of the needle in the collecting enclosure and to identify a type associated with the needle. An accounted-for-needle count associated with the detected needle type is updated based on said identifying.

DESCRIPTION OF DRAWINGS

FIG. 12 depicts example thread cutting devices.

Figure 18:
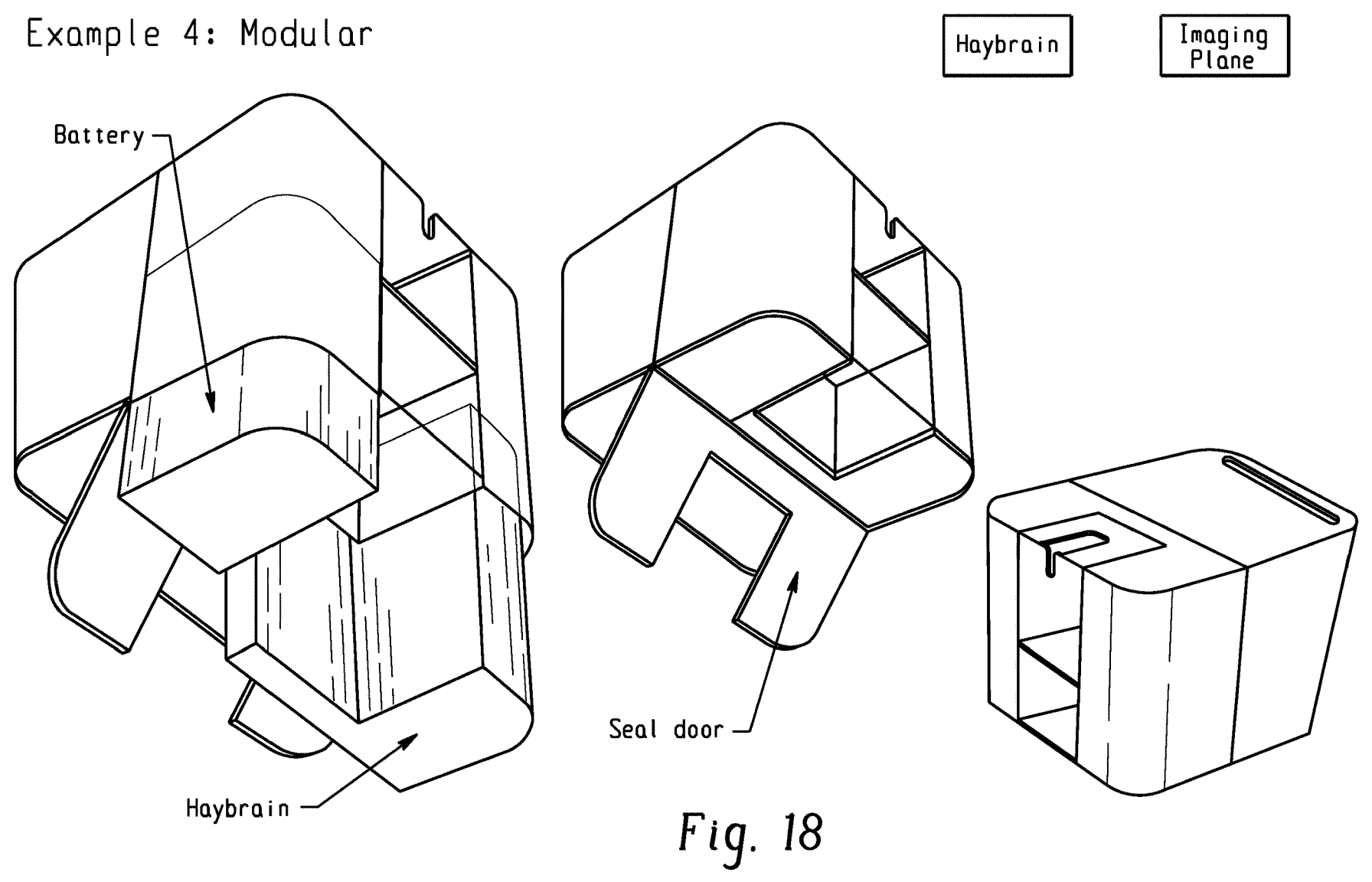

FIGS. 13-20 depict additional examples of counting apparatus shapes and physical arrangements.

DETAILED DESCRIPTION

Figure 1:
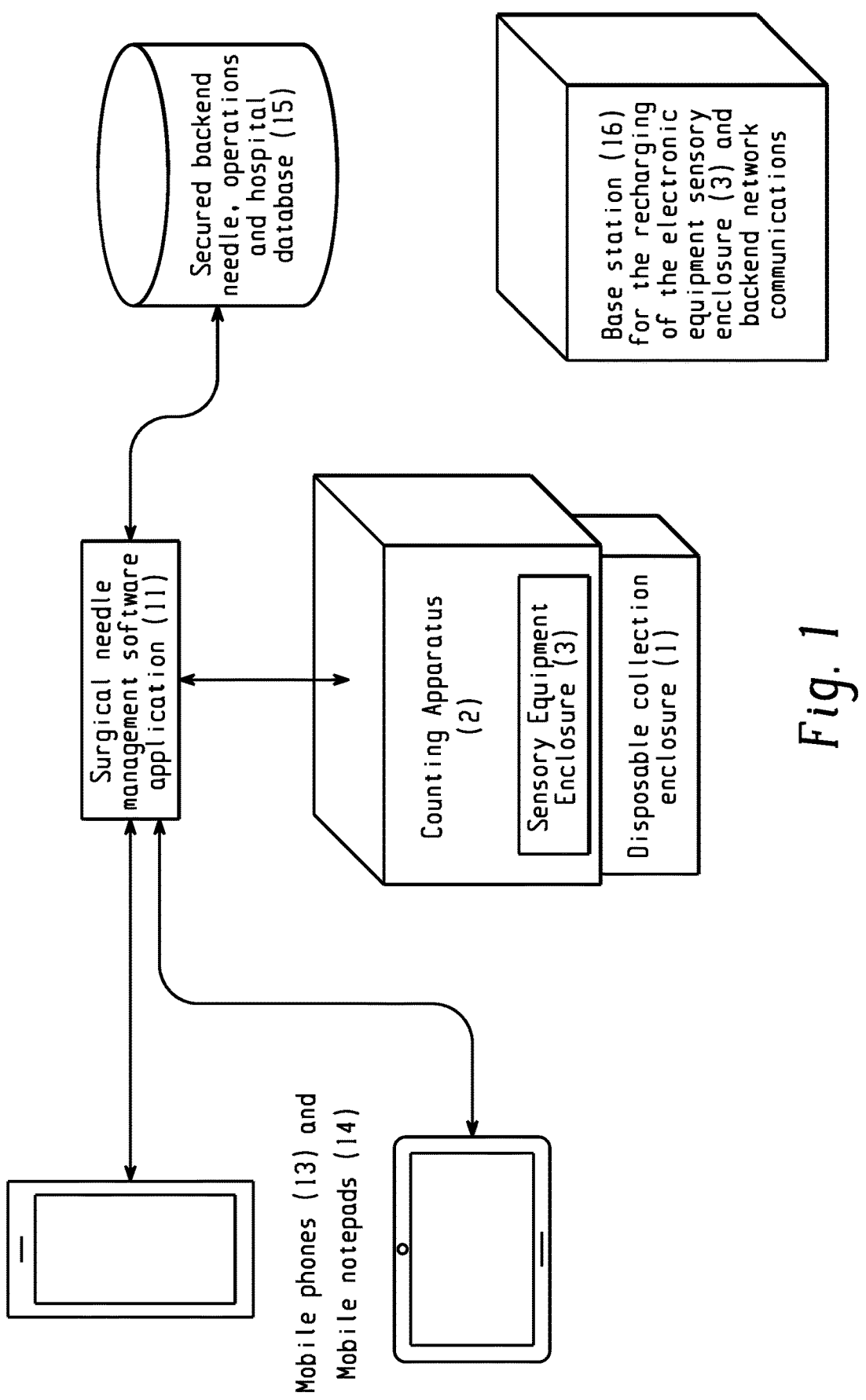
FIG. 1 is a diagram depicting an example surgical counting device for an operating room.

In the operating room, there are a variety of items, many of which are very small, that must be tracked. For example, almost every type of operation requires a variety of surgical succors and the associated succor needles which are sharp. There are medical risks to the patient if a needle is left in the patient, and there are risks to the medical staff if all needles are not accounted for. Sharps may also stick or injure the medical staff. Often at the conclusion of an operation, medical staff needs to accurately and statistically check the status of operating room items, such as the number of needles that entered the surgical field for potential use, the number of needles that were actually used during the surgical procedure, the number of needles that were unpacked and placed in the surgical field, and the number of total needles used in the procedure plus unpacked in the field to be disposed in the appropriate sharps disposal. At present, hospitals typically use manual counting methods for tracking operating room items (e.g., counting surgical needles on a white board or similar manual tracking chart). Manual tracking and counting process is time consuming and laborious. It is also prone to errors, which could result in injuries.

System and methods as described herein provide a tracking device and associated software for an operating room, which can provide a variety of functions including counting the number of used surgical succor needles that enter the sterile field. In embodiments, systems track counts of different item types used during the operation, saving time and labor, and avoiding errors that may result from manual counting. Certain systems and methods can reduce a number of handoff steps for operating room personnel (e.g., in a workflow between a surgeon and the scrub nurse). In such an example, when the surgeon is done with a given succor/needle, the surgeon is able to place the needle in the counting apparatus and get positive indication that the needle was accounted for and secured in a safe sharps collection container. Certain systems and methods are configured to detect needles captured ranging from 0.5 mm to 60 mm in chord width. Those needles may be of a variety of different shapes and types. For example, needle shapes can include a range from ⅝ circle to straight and multicurve needles. Systems and methods may be configured to detect a range of needle point types (e.g., sharp and blunt taper points, cutting and reverse cutting edges).

In embodiments, a set of items (e.g., all succor needles entering the sterile field for prep and all needles used in the surgery) are accounted for and tracked. For example, during the operation, a surgical needle management software application is integrated with scanning functionality, such as those included on a mobile device (e.g., a tablet or a smart phone) or a handheld barcode scanner. Through that scanning functionality, needle packages introduced to the surgical field are tracked. Further, automatically needle sensing of a collection apparatus keeps a surgically used needle count. As a surgeon or other operating room personnel drop used needle into the collection apparatus, the used needle is counted, and in some instances identified by type (and in some instances connected suture material type), such that it can be reduced from the count of surgical needles in the sterile field. This provides assurances that needles are not left in the patient before closure and that needles are not left in the surgical field (e.g., on the surgical floor, the operating room table) where they could risk medical staff health. Once an operation is closed, a collection enclosure of the collection apparatus can be disposed safely in the appropriate sharps repository assuring safety of medical staff from infection resulting from sticks from sharps. Systems and methods herein may also provide accuracy and automation efficiencies in the closure process of an operating procedure, reducing risk to the patient and operating staff while reducing costs and time in completing the surgical procedure and shortening the turnover time for use of the operating room.

FIG. 1 is a diagram depicting an example surgical counting device for an operating room. The device includes a removable, disposable collecting enclosure 1 for receiving objects (e.g., disposed needles, sharps, sponges) in an operating room. While systems and methods described herein can detect, identify, and/or count a wide variety of objects, certain examples herein are described in the context of counting surgical needles (e.g., suture needles) for simplicity. A counting apparatus 2 includes a sensor 3 for determining when an needle is dropped into the removable collecting enclosure 1. The counting apparatus 2 is configured to maintain a count of needles introduced into a surgical field associated with the operating room (e.g., by scanning packages of needles (e.g., a barcode, OCR'd text on a needle package) as those packages of needles are opened. The counting apparatus 2 is further configured to maintain a count of accounted for needles (e.g., needles detected by the sensor 3 as entering the removable collecting enclosure 1). The count of needles introduced in the surgical field can then be compared to the count of accounted for needles to make sure that all needles are accounted for prior to closing the surgical operation (e.g., to ensure that no needles are left in a patient or in an uncontrolled area where inadvertent needle sticks of a patient, operating room staff, or other hospital staff (e.g., cleaning staff) could occur).

The counting apparatus 2 utilizes surgical needle management software 11 for maintaining counts of needles introduced into the surgical field and needles accounted for at disposal, such as when those needles are dropped into the removable collecting enclosure 1. That software 11 may be executed using data processors contained at one or multiple locations, including in or on the counting apparatus 2, at a remote base station 16 that receives signals (e.g., wirelessly transmitted signals) from the counting apparatus, and at one or more remote computing devices (e.g., mobile phones 13 or tablet devices 14). The counting device 2 and associated software 11 may further communicate data (e.g., counts of needles) to a database 15 that retains that data long term for audit purposes. The retained data may further be used for statistical analysis and machine learning regarding how and when needles, succors, and other implementations are used and consumed during a surgical procedure. In embodiments, individual transactions of a surgical procedure (e.g., the introduction of a pack of needles of a certain type into the surgical field, a count of a needle of type X into the removable collecting enclosure, a count of a needle of type Y into the removable collecting enclosure, the disposal of the remainder of n unused needles in the pack previously scanned into the surgical field) are stored in the database 15. That data can be accessed at a later date, such as part of an incident investigation, operation quality evaluation, or for training purposes. Needle count data can also be transmitted to devices 13, 14 for display during a surgical procedure.

Systems and methods herein may further comprise a base station 16 to which certain of the previously described components may be permanently or temporarily attached, such as for the purpose of charging batteries. In embodiments the base station 16 takes the form of a vertical stand, while in other embodiments the base station 16 is an apparatus that is placed horizontally on a surface, such as a table, a stand, or the floor. The base station 16 may be connected to the electrical grid via a plug when operational. In embodiments, the base station 16 may have batteries of its own that facilitate charging of other sub-devices of the system (e.g., sensory equipment removably connected to the counting apparatus at 3) and performing other operations while disconnected from the electrical grid. In embodiments, the base station 16 may include network connectivity equipment, such as a network hub or wireless router for connecting devices of the system together and to a larger outside network. For example, the data processor executing the surgical needle management software application 11 (e.g., as a component of the counting apparatus) and the mobile devices 13, 14 may connect to the base station via a wireless connection through a router at the base station 16. In embodiments, the base station 16 may limit connections to only devices in the present operating room, to avoid cross talk of devices across nearby operating rooms that could result in erroneous communications. The base station may communicate to a larger network, including a network that expands beyond the operating room, such as the Internet. For example, the secure backend database 15 may be physically located outside of the operating room, at an onsite or offsite server or on a cloud server. The base station 16 network hardware enables data (e.g., counts of needles introduced into the surgical field, counts of needles accounted for during disposal, and associated time stamps) to be transmitted in real time or as an after-operation log file to the database 15 for storage and future access and analysis.

In embodiments, certain components may be configured to be present in the surgical field in a sterilized state, while other components may be configured to be unsterilized but shielded from the surgical field to prevent contamination. For example, the sensor 3 may be a non-disposable sensor that is desired to be used across multiple surgical procedures. But the presence of electronic equipment in the sensor 3 may make typical sterilization techniques (e.g., autoclaving) inappropriate. In such an example, the sensor 3 may be placed inside an enclosure within the counting apparatus 2 in a manner that avoids any direct or indirect contact with sterile surfaces within the surgical field. In addition to sensors 3, components containing data processing hardware and software (e.g., surgical needle management software and data processors for executing that software) may be removably introduced into secure enclosures in the counting apparatus so as to maintain sterile status of the counting device.

Figure 2:
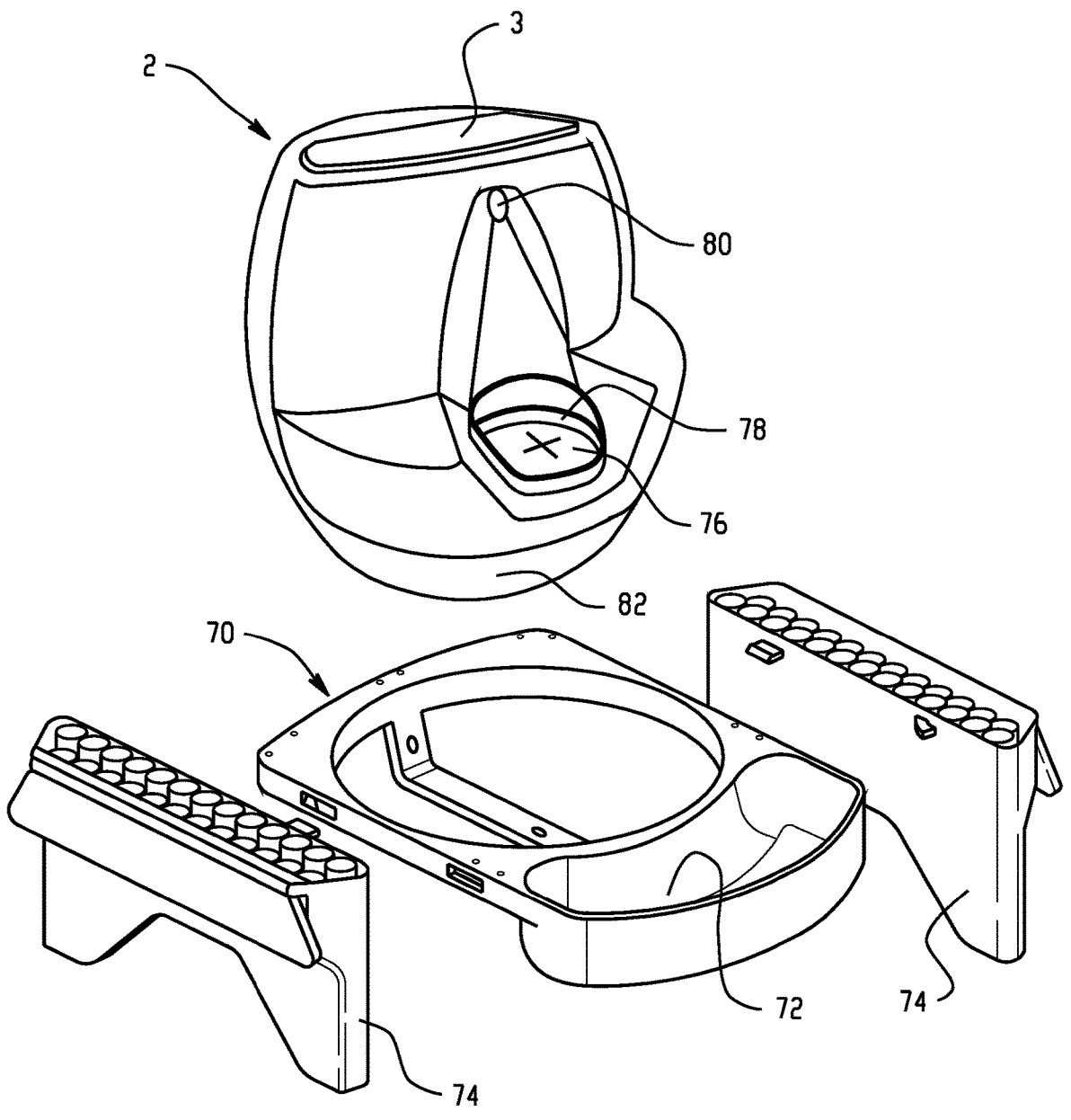
FIG. 2 is a diagram depicting a vision-system counting apparatus.

A counting apparatus may take a variety of forms. FIG. 2 is a diagram depicting a vision-system counting apparatus. The counting apparatus includes a vision system for determining that an object, such as surgical needles or sharps, has been received, and in embodiments that vision system is used to identify characteristics of the received, for example, needle, such as size, shape, and even type. In one embodiment, the surgical needle management software application 11 includes a model trained using a machine learning technique. In embodiments, that machine learning technique processes large numbers of needle images (e.g., hundreds, thousands, millions, billions) where each of those images is associated with metadata, such as the size, shape, material, needle type, associated with that needle. The software application's model (e.g., a neural network model) is trained based on those tagged images so as to recognize those characteristics of future needles captured via its vision system (e.g., via a camera in the orb-shaped counting apparatus).

With reference to FIG. 2, the counting apparatus 2 is formed from a housing that is configured to sit within a support structure 70, which may be connected to a support structure such as to an arm extending from a wheeled vertical stand. The support structure 70 includes a recess for the counting apparatus to sit in as well as a disposal area 72 for depositing waste, such as suture material removed from the end of a needle prior to depositing the needle in the counting device, such as using a cutting device attached (see FIG. 12) to one of the counting apparatus 2, the support structure 70, the movable stand, or elsewhere in the surgical environment. In embodiments, a system may include one or more sharps caddies 74 attached to the support structure for depositing and accounting for certain sharps that are not an appropriate size for depositing into the counting device 2, where for example, the caddies 74 may be formed of hard plastic that prevents penetration by sharps, such as scalpels, deposited sharp end down into the caddies 74.

Figure 3:
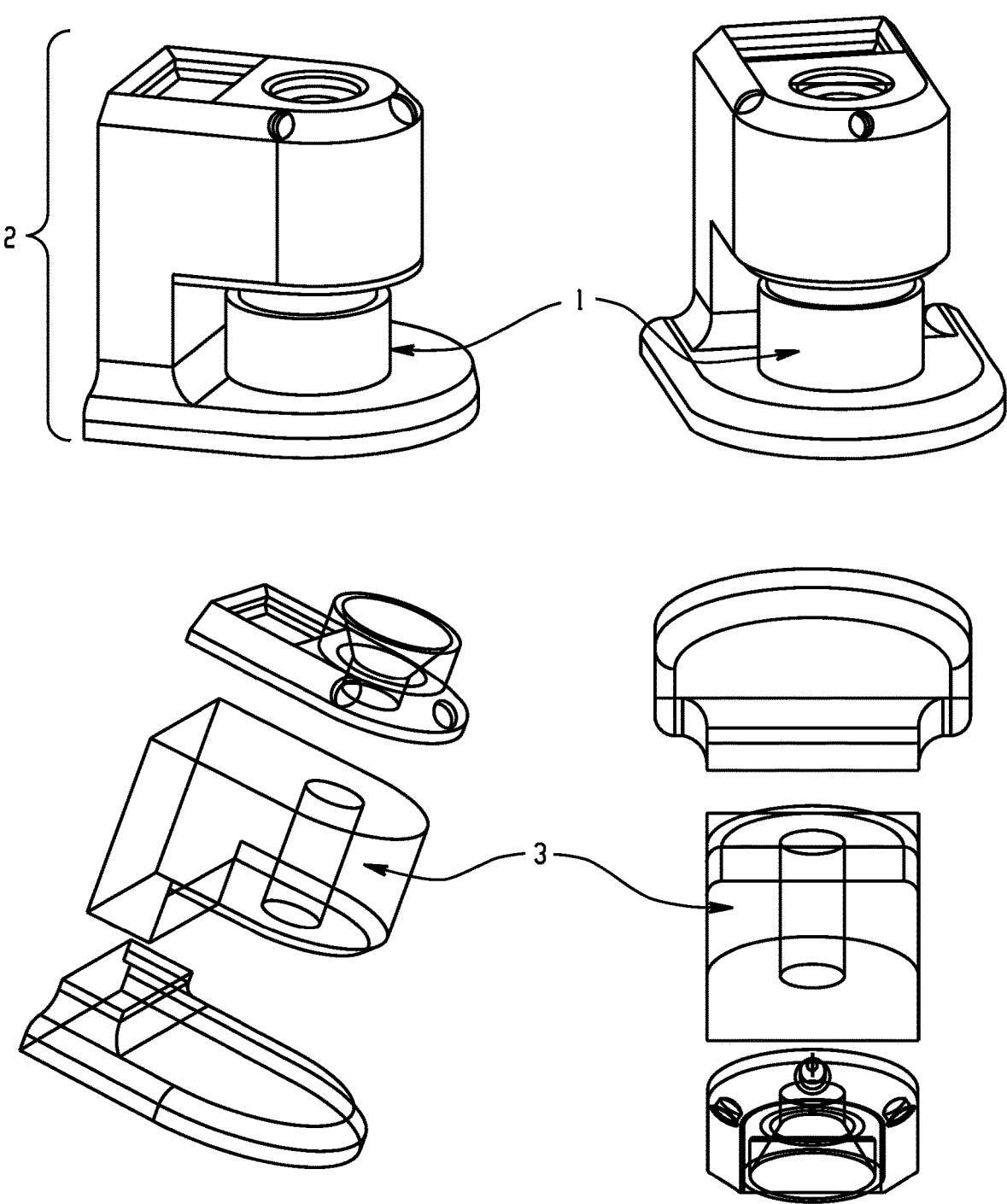
FIG. 3 depicts an alternate form of a counting apparatus that utilizes an inductive sensor for detecting the presence of needles and characteristics of those needles.

In the example of FIG. 3, the counting device 2 includes sensor equipment 3 enclosed within the counting device 2 so as to not contaminate the surgical field, even if the sensor equipment 3 is not sterile. In operation, a needle is placed by a surgeon or operating room tech onto a target pad 76. The counting device 2 may detect the presence of a needle there automatically, such as via a pressure sensor on the pad 76, an inductive sensor present on the ring 78 surrounding the pad 76, or through use of a camera (e.g., a camera near light source 80 for use in darkened operating rooms). The presence of a needle on the pad 76 may also be manually indicated to the counting device 2 by a button press, voice command, or gesture. When a needle is deemed present on the target pad 76, a mechanical mechanism rotates the 76 to the back side of the device, under the sensor equipment 3, while a second target pad is rotated to the front depicted position. A magnet under the first pad may be energized to aid in holding the needle on the first pad. The first target pad is now positioned in a light controlled environment (e.g., a tube into which polarized light is projected while shielding the controlled environment from outside light). A camera (e.g., a camera looking down on the controlled environment, focused based on a known reference printed on the target pad such as microdots) takes one or more images of the needle on the first pad, where the images are used for recognition of the presence of the needle, characteristics of the needle, and/or the type of the needle (e.g., by comparing characteristics of the needle to those of known needle types in a database, by image recognition provided by a machine-learning trained model). When a subsequent needle is confirmed on the second pad, the pads are again rotated such that the first pad returns to the front position for receipt of another needle. In that rotation process from the controlled image capture environment, the needle may be scraped, wiped, or otherwise removed (e.g., the magnet is deenergized to aid in removal) from the first pad such that the needle falls into its permanent collection enclosure 82 at the bottom 82 of the counting device 2 for subsequent disposal (e.g., the entire sealed bottom portion 82, or the entire counting device with sensor equipment 3 removed is disposed as a sharps container).

Figure 4A:
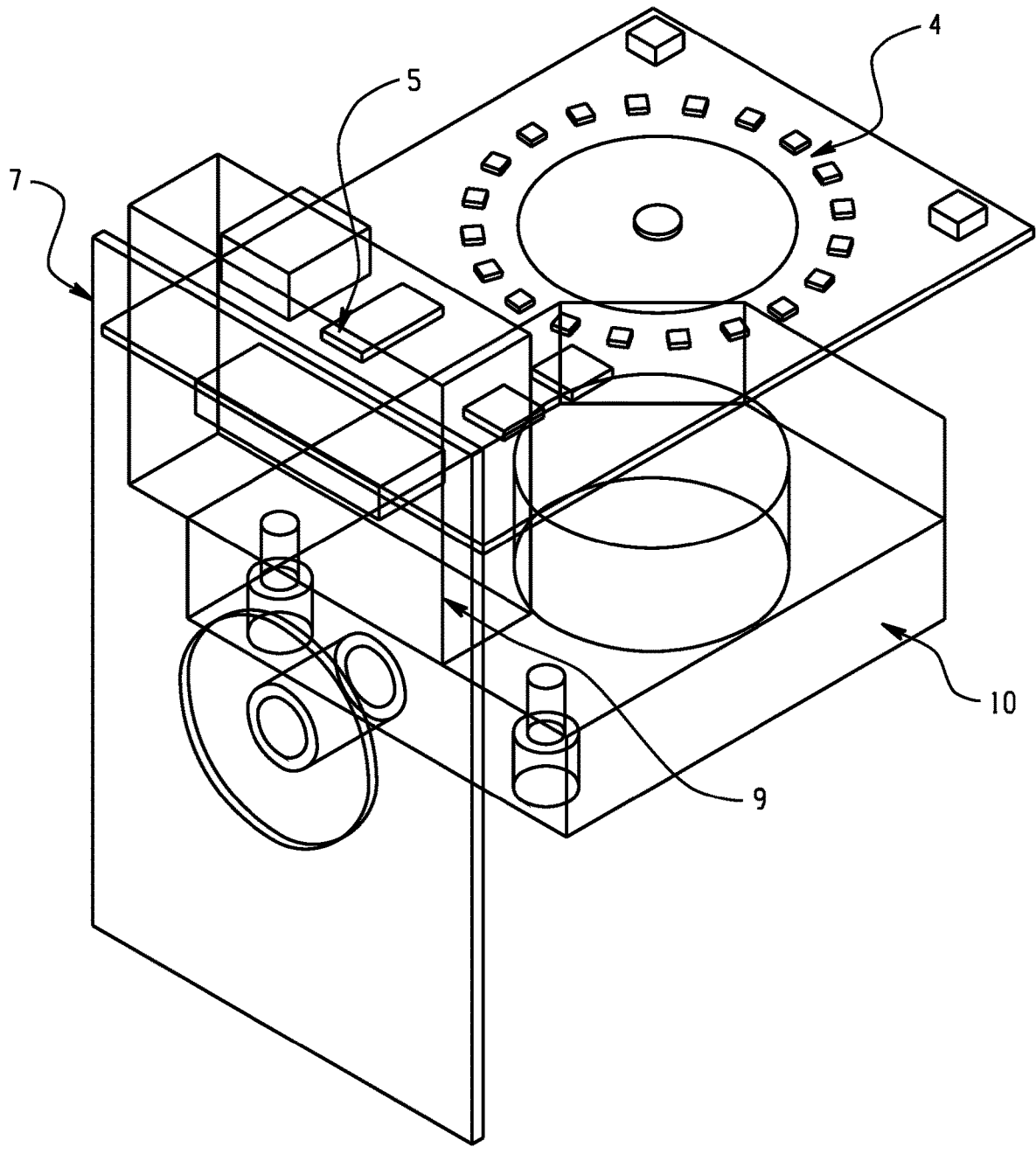
FIGS. 4A-4B depict another form of a counting apparatus including communication circuitry, rechargeable power supply and metal detecting sensors.
Figure 4B:
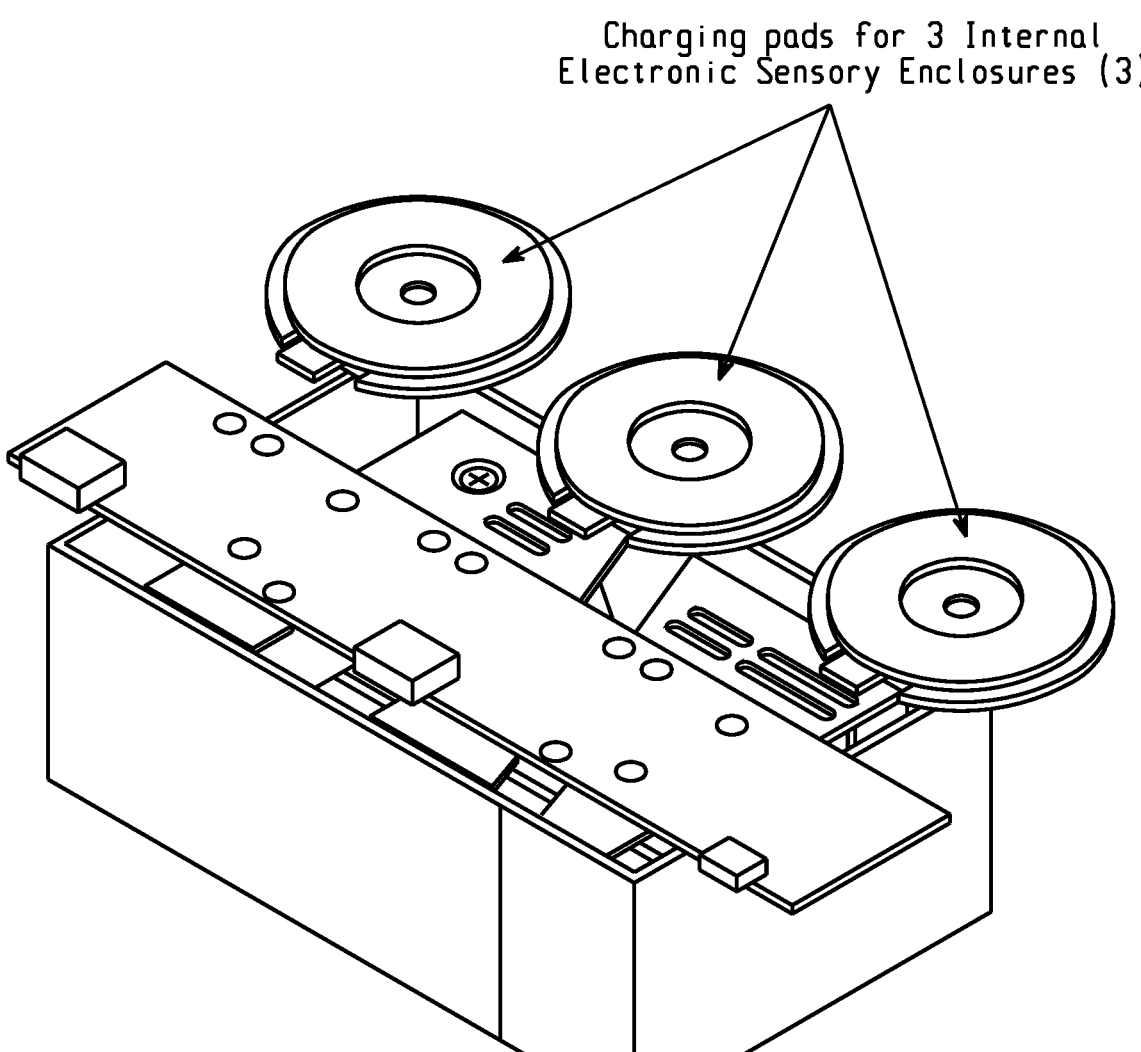

FIGS. 3 and 4 depict an alternate form of a counting apparatus that utilizes an inductive sensor for detecting the presence of needles and characteristics of those needles (e.g., size, shape, material, type). The operating room needle counting apparatus and software application of FIGS. 3 and 4 includes a disposable collection enclosure 1, a collecting appliance 2 for accommodating the collection enclosure 1, and an electronic sensory equipment enclosure 3 for sensing surgical suture needles after use in a surgical procedure. The electronic sensory equipment enclosure 3 is installed within the collecting appliance 2. In this example, the sensory equipment enclosure contains hardware for sensing needles via an inductive sensor therein. The enclosure further includes visual indicators 4 for power and charging level indication. The enclosure further includes mechanisms for issuing alerts (e.g., visual or audio alerts via lights or a display), indicating events including needle detection events when a needle is detected to have been dropped into the collection enclosure 1. The apparatus includes a power supply 6 and communication circuitry 7 (e.g., for Blue-Tooth and Near Field Communications) for communicating with a software management platform 8. The apparatus includes one or more inductive ring sensors or other metal detecting sensors 10. One or more of the sensory equipment 3, the visual indicator or display 4, the speaker 5, and the inductive ring sensor 10 are connected to a rechargeable power supply 9.

The in the sterile field collecting appliance 2 communicates to a surgical needle management software application 11 running within the operating room. This application collects needle count information as gathered by the collecting appliance 2 and its internal sensor equipment 3 reflecting this data in its surgical needle usage database 12 per operational procedure. In one example, surgical needle management software application 11 runs on both secured mobile devices 13 and mobile notepads 14 (e.g., iphone, Android, or other mobile platform based devices) and stores data on a secured backend database 15. The surgical needle management software application 11 also tracks the usage of the surgical needle collection enclosure(s) 1 used in the procedure and provides visual usage and needle counts of needles entering the field and placed in the collecting appliance 2 after surgical use. This information may be displayed on the mobile devices 13 and mobile notepads 14 and other devices (e.g., a wall-mounted monitor) that are paired with the management software application 11.

In addition, to automated detection and counting of needles via the one or more sensors 3, needle counts can be corrected through manual intervention, such as via controls on the counting device or via user interfaces on the mobile device 13 and mobile notepad 14 via the surgical needle management software application 11. While, in examples, the collection of data about the surgical needle count used in the operation is ultimately stored in the secured backend database 15, connectivity to that database need not be maintained at all times (or at all). In embodiments, the counting appliance 2 includes local data memory and storage for short term data storage (e.g., during network communication faults, power outages) or for long term storage in examples where the database 15 is not used. This can prevent interruptions to surgical procedures in the event of certain faults.

A system may further include a base station 16 configured for recharging of the electronic equipment sensory enclosure 3. In embodiments, the base station may include network connectivity hardware, such as for wireless communication with the collecting appliance and wired or wireless communication with an outside network (e.g., an external network having connectivity to the database 15).

The counting apparatus 2 may be autoclavable, and the electronic sensory equipment enclosure 3 can be easily assembled and disassembled into the sealed collecting appliance 2, sealing the exposed sterile collecting appliance 2 before being placed into the surgical field. The removable disposable collection enclosure 1 can be removed and replaced with an additional disposable collection enclosure 1 to provide additional capture capacity. In embodiments, the counting apparatus 2 may maintain a per-enclosure count of needles held therein as well as counts for the larger operation procedure. In embodiments, per-enclosure counts (e.g., total needles, total needles per detected needle type) may be matched a particular disposable enclosure 1 via reading of a barcode microdots or printed alphanumeric text that indicates a unique identifier of the enclosure 1. In embodiments, the per-enclosure counts may be used to issue an alert when the current enclosure 1 is full or near full. The alert may be issued when a needle threshold is reached (e.g., this enclosure can hold up to x needles of any type). The alert threshold may be adjusted, in embodiments, based on the types of needles detected as being inserted therein, where that threshold may be adjusted up when smaller needles are detected because those smaller needles will take up less room in the enclosure 1. In embodiments, the threshold may be adjusted to take into account the counts of different types of needles that have been detected to be inserted therein.

Figure 5:
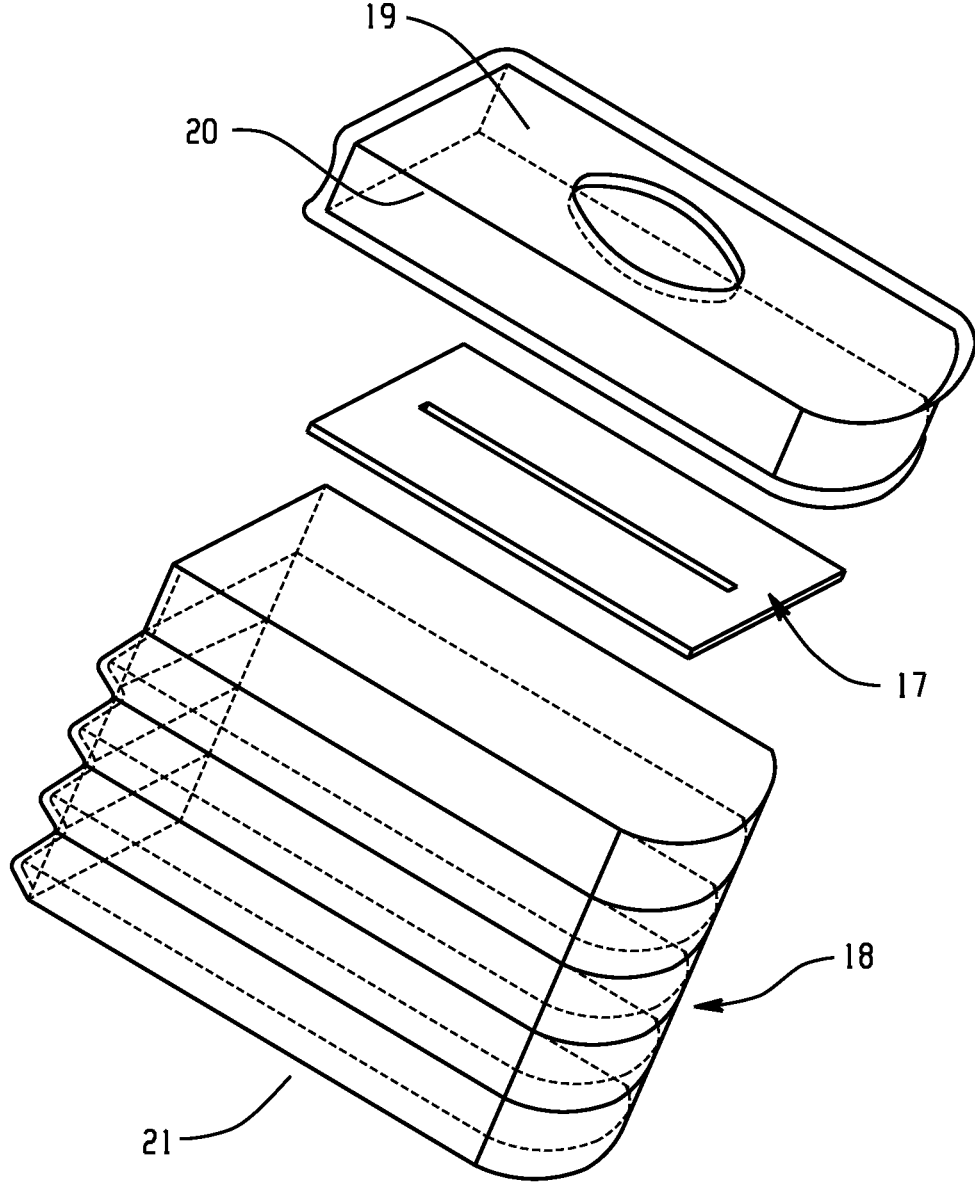
FIG. 5 is a diagram depicting an example disposable collection enclosure 1.

The disposable collection enclosure 1 may take a variety of forms. For example, the enclosure 1 may be a structure configured to be held in place in the counting apparatus 2 as a liner in a bowl structure, via clips, via tongue and groove structures, or by being set within a recess in the housing of the counting apparatus 2. FIG. 5 is a diagram depicting an example disposable collection enclosure 1. The enclosure 1 may be manufactured via a sterilized process and of sterilized materials and shipped in sterile packaging. The disposable collection enclosure includes a self-sealing mechanism 17 that prevents the removal or escape of needles when the enclosure 1 is when removed from the collecting appliance 2. In embodiments, the cover 19 and the self-sealing mechanism can be traversed by a camera (e.g., a fiberoptic camera) to image needles contained within the enclosure 1, such as for automated counting via image recognition, for semiautomatic counsel via display and touch counting on a remote touch display, or for retention for recollection as part of a future inquiry (e.g., an audit or investigation). The enclosure 1 may be formed of a robust plastic or rubber material that is resistant to piercing by needles or other sharps therein, providing a safe, disposable sharps disposal medium. In embodiments, the material may be transparent or translucent such that objects stored therein may be visible from outside of the enclosure 1. In one embodiment the sterile disposable receptacle 1 can expand and collapse 18 in an accordion fashion, minimizing size during storage, transport, and disposal. The receptacle has a self-sealing interface 17 and a cover 19 having grooves 20 on its side for interfacing with tongues on the counting apparatus 2 (or vice versa) for temporary attachment to counting apparatus 2. In embodiments, a magnet 21 may be positioned at the bottom of the enclosure 1 so as to orient deposited needles (e.g., to keep needles from being retained through the opening in the cover 19, to position needles for optimum sensing, to prevent needles from escaping the enclosure 1). In embodiments, a magnet may be positioned in a housing of the counting apparatus 2 (e.g., below where the enclosure 1 is placed) to perform the same function through the walls of the enclosure 1. In one embodiment, the magnet's effect is periodically interrupted to facilitate movement of a needle (e.g., the magnet's surface is scraped or an electromagnet is powered down), such as after detection is complete (e.g., after the needle is imaged by a camera).

The disposable collection enclosure 1 of the systems and methods can be conveniently be removed from the collection apparatus 2 and replaced with a new disposable collection enclosure 1. The surgical needle management software application 11 can uniquely track the disposable collection enclosure 1 with the scanned unique identifier 12 for each collection enclosure 1 as the enclosure is attached to the collection apparatus 2. Furthermore, as described above, the surgical needle management software application 11 may track surgical needles that have been prepped in the surgical field for potential surgical usage, through integrated scanning and succor needle identification and storage of the information in the surgical needle usage database 13.

Figure 6:
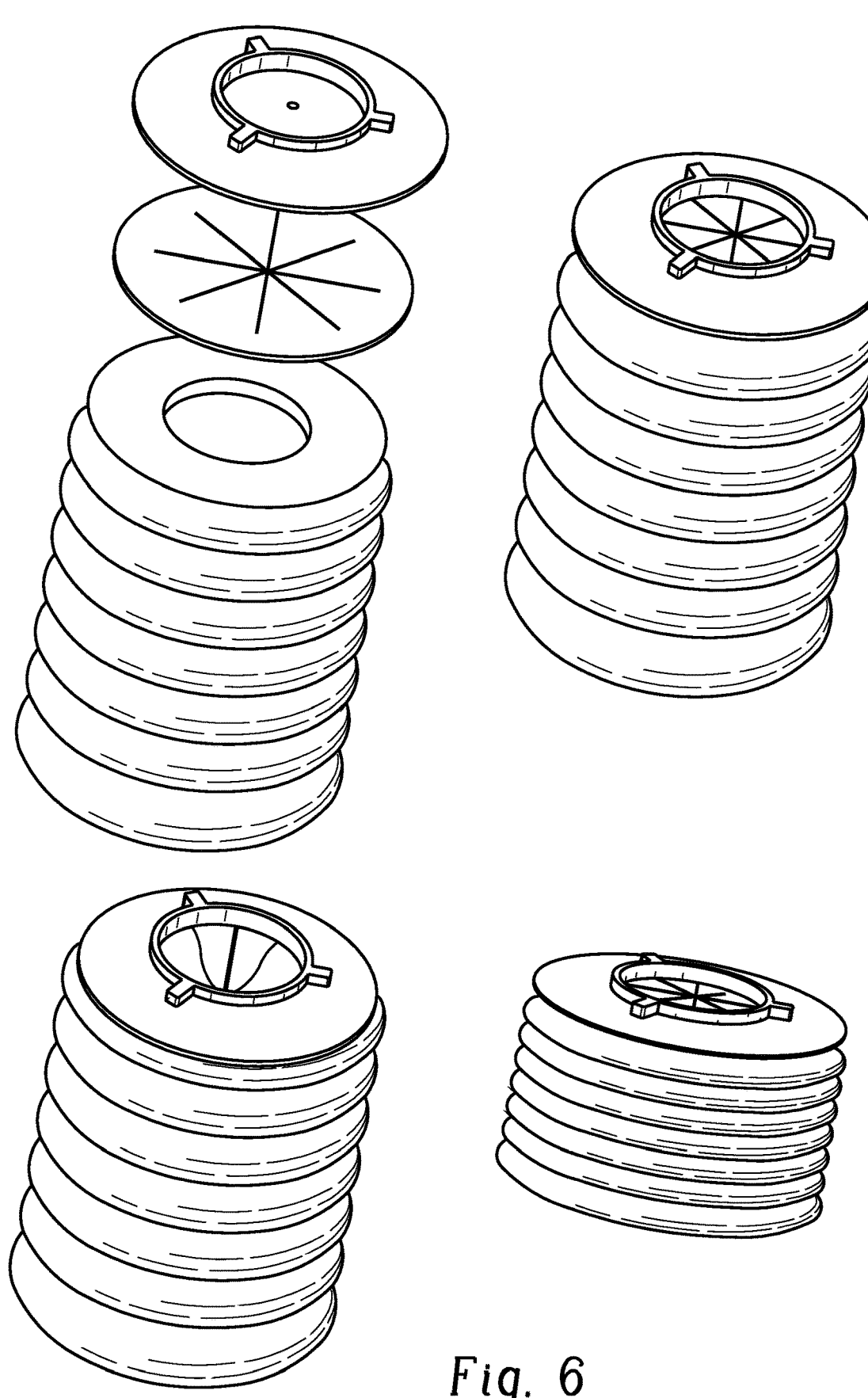
FIG. 6 displays a round, collapsible enclosure in component and assembled form, where the self-sealing interface is perforated in a star-shape configuration.
Figure 7:
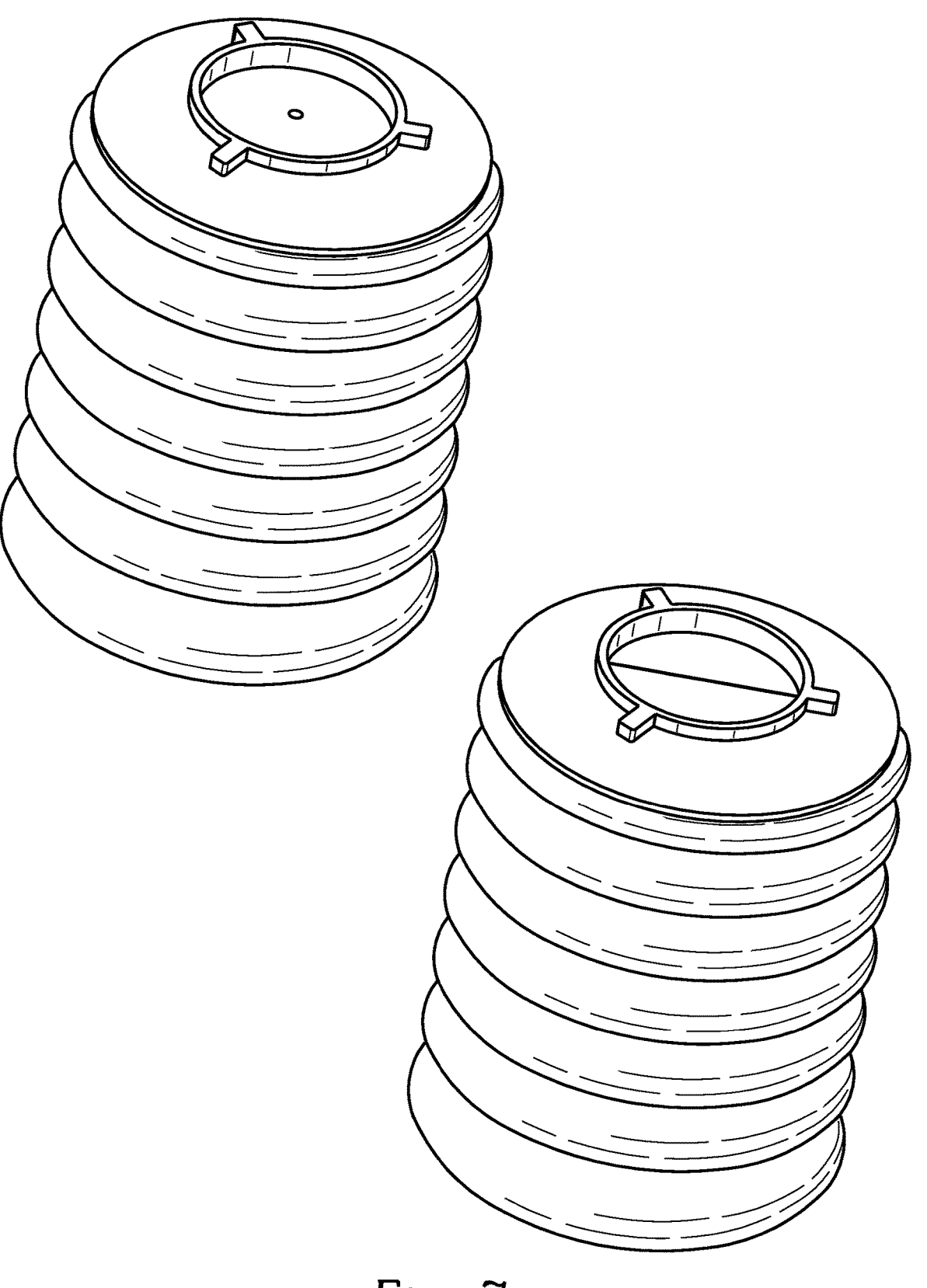
FIG. 7 illustrates alternate self-sealing interface shapes including a point-shaped opening and a line-shaped opening.

Disposable collection enclosures can take a wide variety of forms. FIG. 6 displays a round, collapsible enclosure in component (top left) and assembled (top right) form, where the self-sealing interface is perforated in a star-shape configuration. Objects, such as needles or other sharps, may be inserted into the container by being pushed through the self-sealing interface as illustrated at bottom left. The enclosure is depicted in its collapsed form at the bottom right. FIG. 7 illustrates alternate self-sealing interface shapes including a point-shaped opening (top left) and a line-shaped opening (bottom right).

Figure 8:
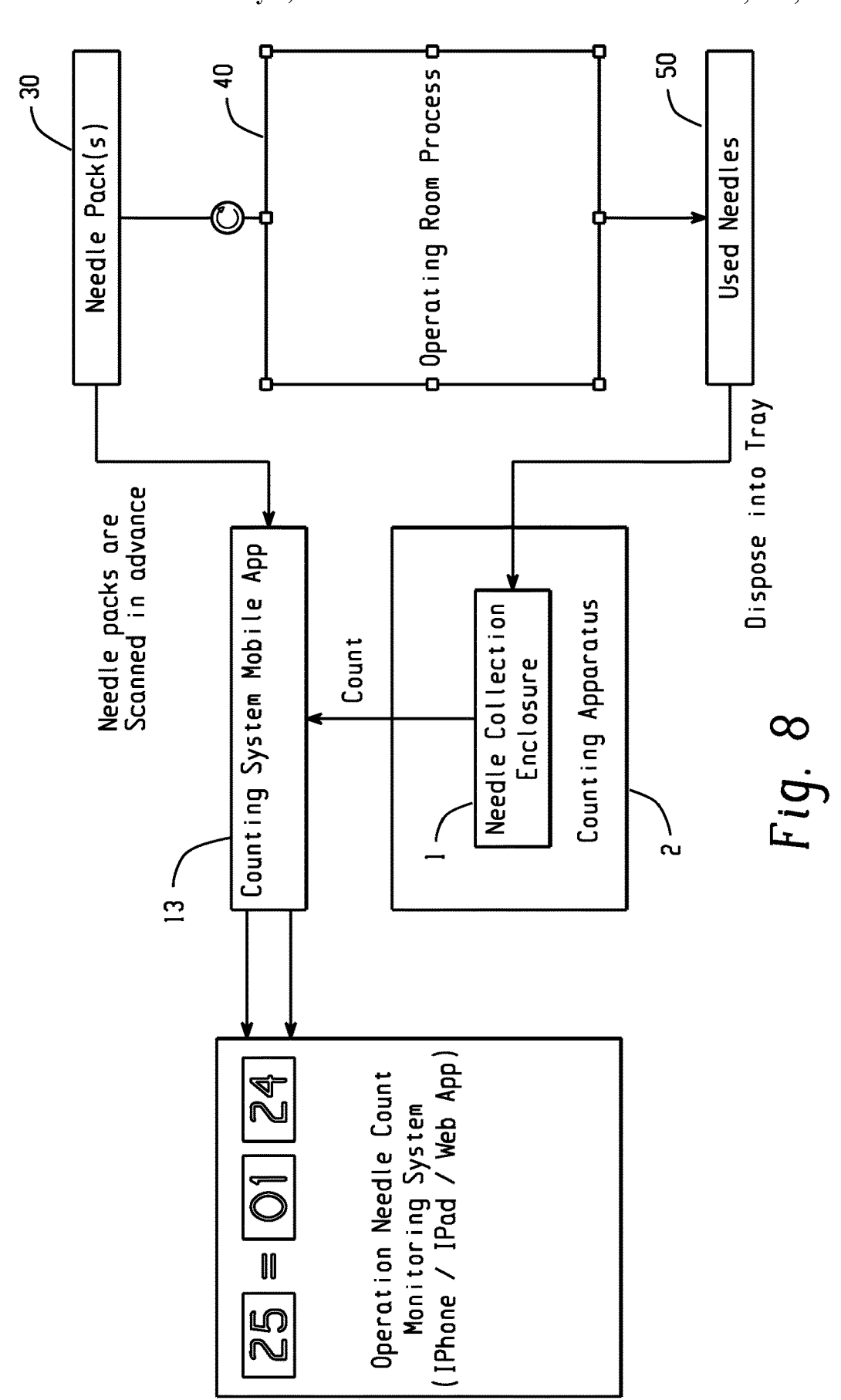
FIG. 8 is a flow diagram depicting an example process for counting objects in a operating room environment.

FIG. 8 is a flow diagram depicting an example process for counting objects in a operating room environment. A counting apparatus 2 includes a needle collection enclosure 1. Needle packs 30 are scanned into the surgical field via a scanning mechanism of a mobile device 13 having a optical, infrared, RFID or other scanner thereon for identifying the pack of needles. For example, a barcode, characters, microdots or other indicia on the pack 30 are read by the mobile device. A determination is made (e.g., by an app on the mobile device 13 or software on the counting apparatus 2) regarding the number of needles in the pack 30 and in some instances the type of needles in the pack. Once scanned into the surgical field, the total number of needles in the pack 30 that is soon to be opened for use must be accounted for by the end of the procedure. Individual needles are extracted from the pack 30 and used in the operating room process 40, such as for performing sutures. Once use of a needle is complete, used needles 50 are deposed into the tray/needle collection enclosure 1 of the counting apparatus 2. The presence and/or of the used needle 50 in the enclosure 1 is detected, and a count of accounted for needles (overall and/or of the detected needle type) is incremented. Counts of accounted for and unaccounted for needles in the surgical field may be stored and displayed at a variety of locations including the mobile device 13, external displays, and other computing devices 14 (e.g., other mobile devices, other computing devices connected via the Internet and accessed via a web-application). The example of FIG. 8 illustrates that 25 needles have been introduced into the surgical field, one of those needles have been detected as entering the enclosure, while 24 needles currently are unaccounted for. Those unaccounted for needles might still be in a partially used pack 30, be currently being used in the operating room process 40 or may otherwise be lost (e.g., in a patient or in the operating room) such that a search is required.

Figure 9:
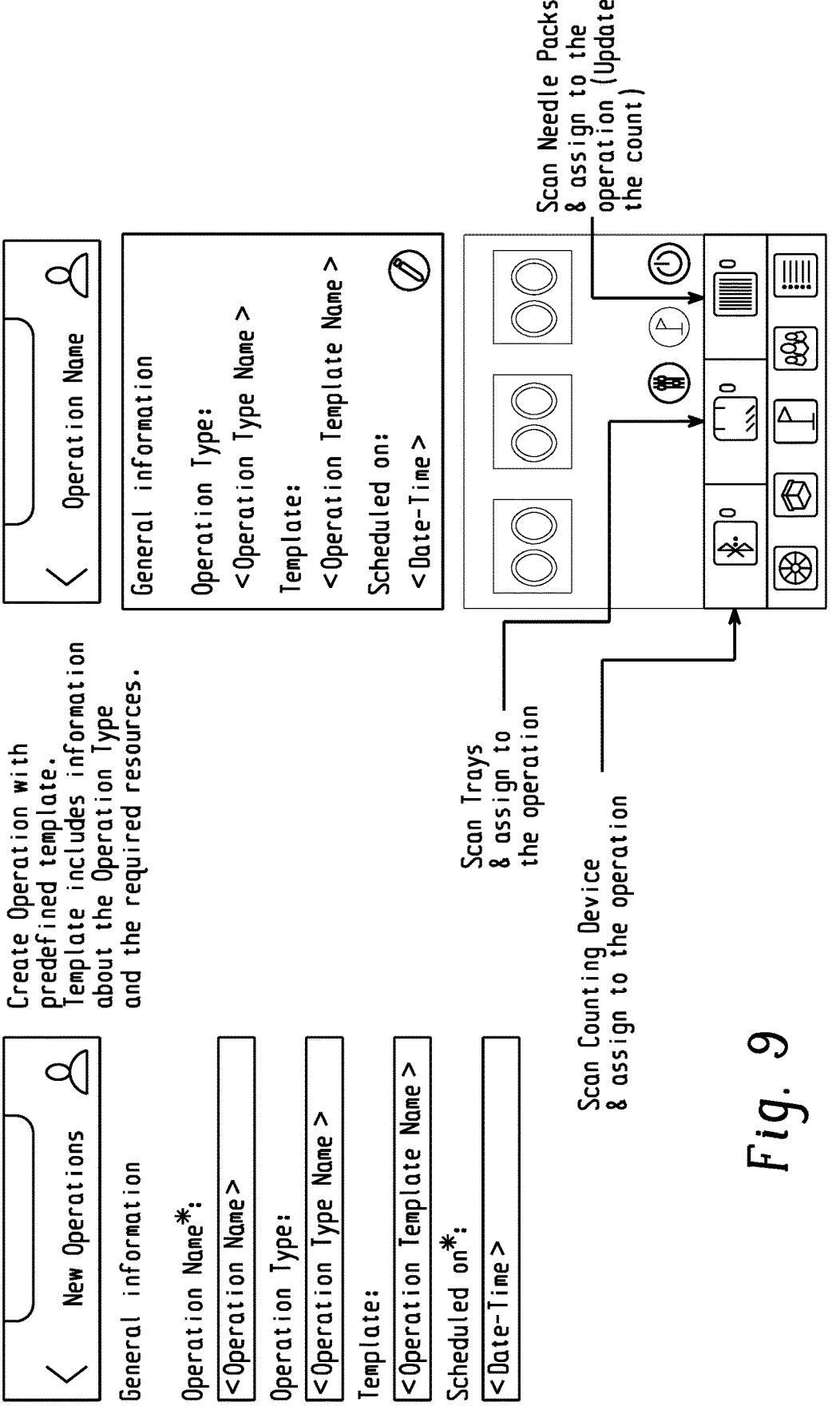
FIG. 9 depicts user interfaces for setting up an operating room procedure and initiating counting of needles in a pack.
Figure 10:
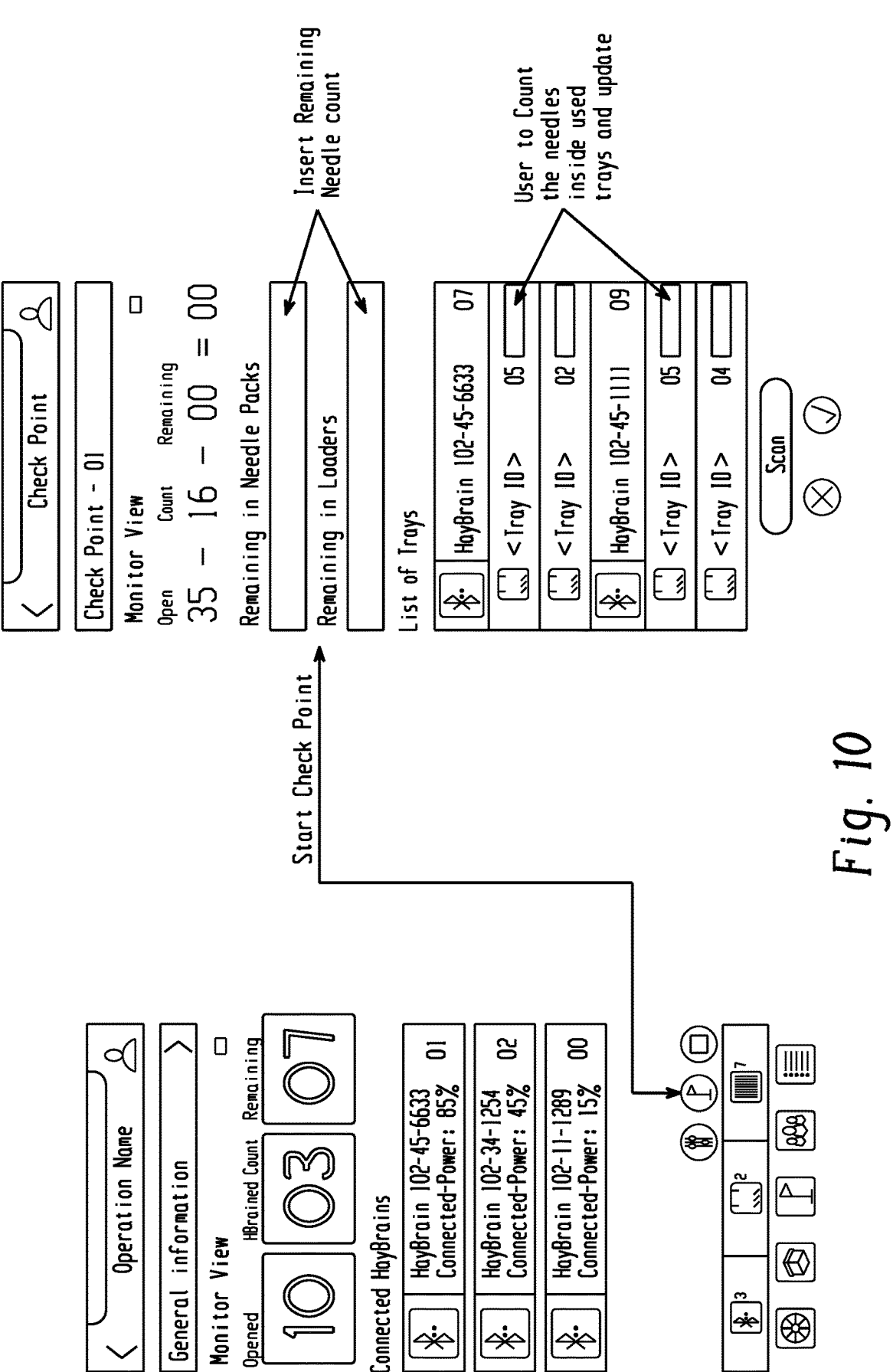
FIG. 10 depicts user interfaces for viewing the counts and for manually adjusting a count.
Figure 11:
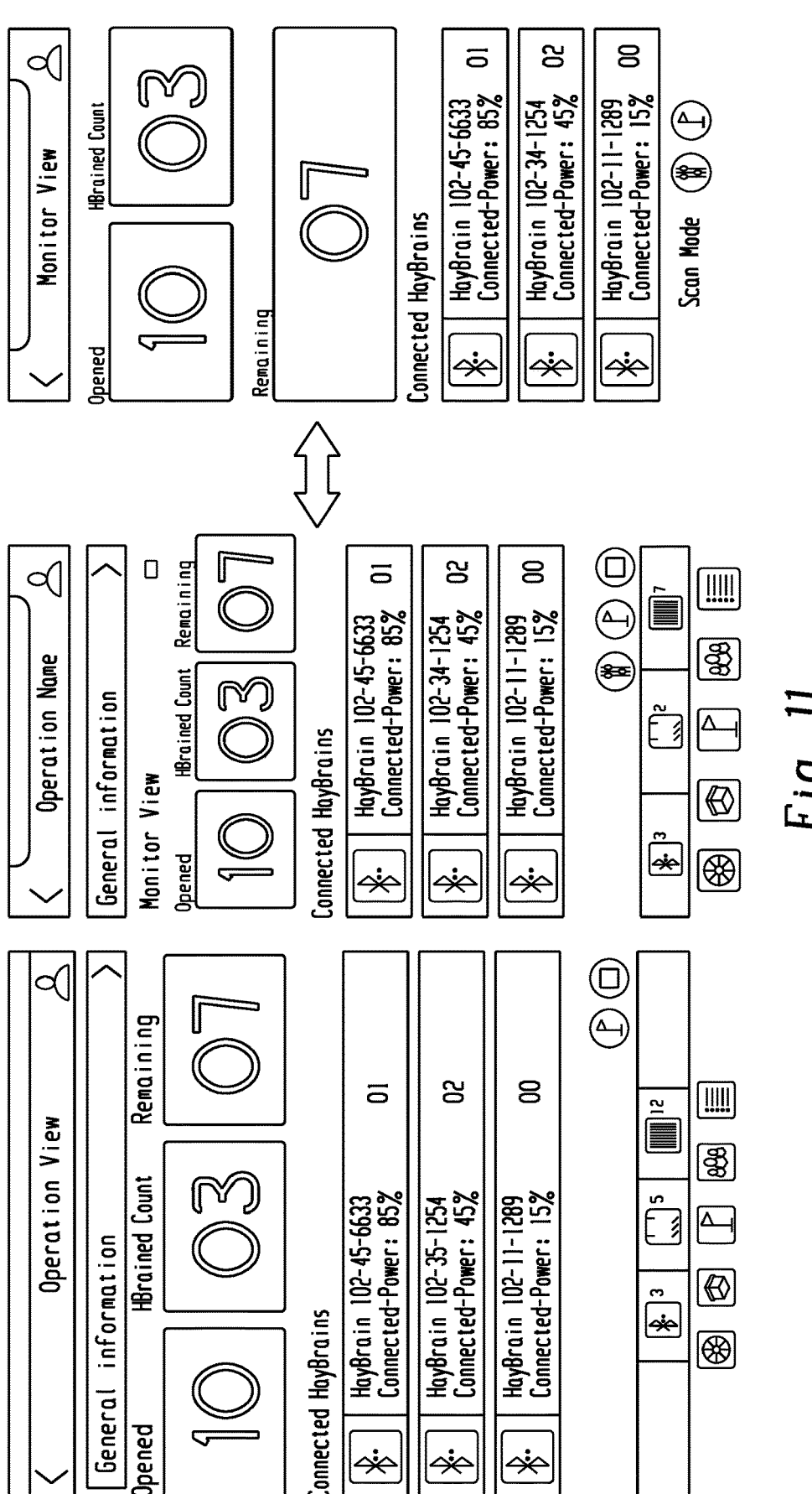
FIG. 11 depicts additional user interfaces in different orientations and arrangements, where per-enclosure counts are depicted for multiple enclosures used during the operation.
Figure 15:
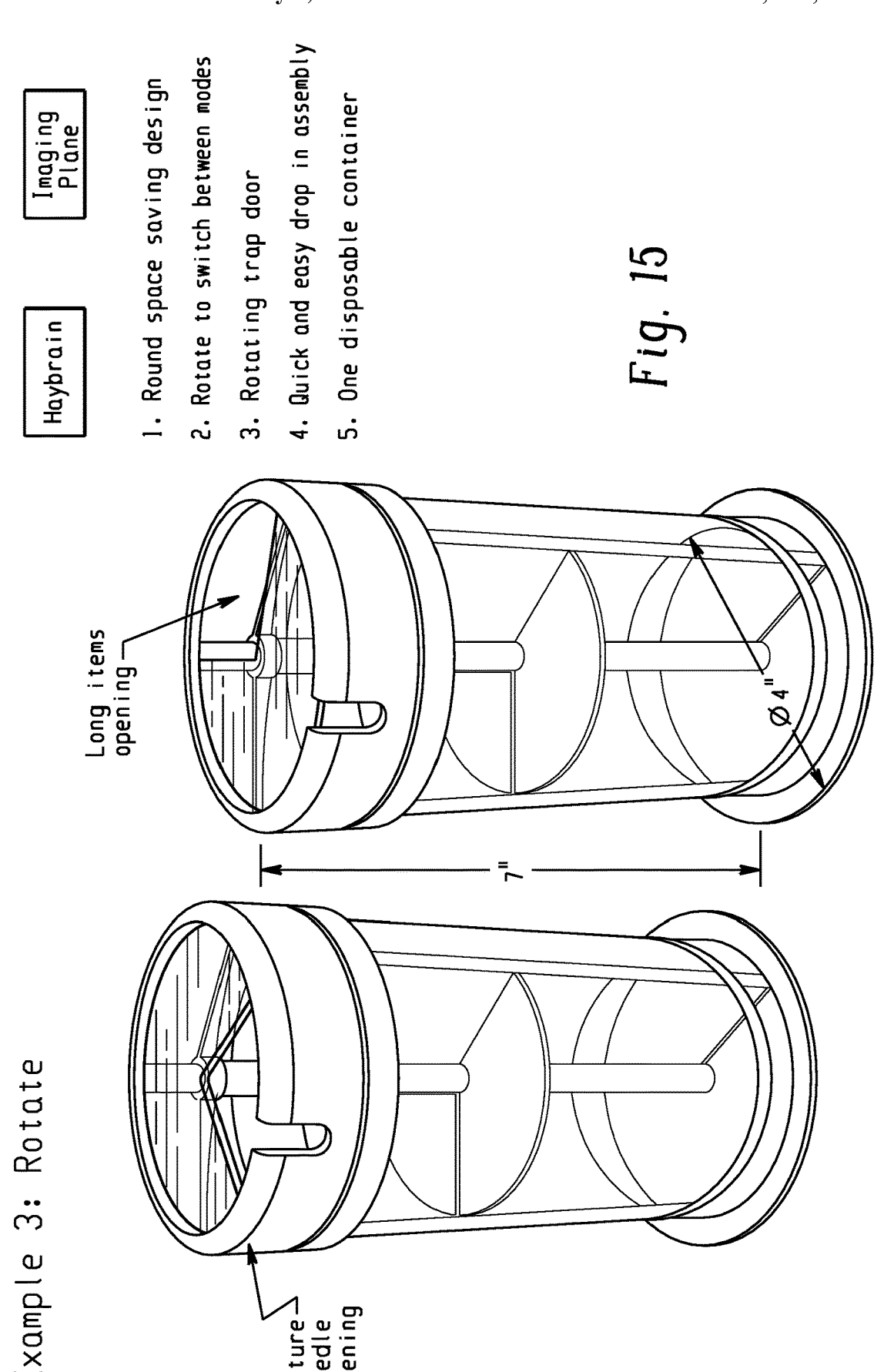
Figure 16:
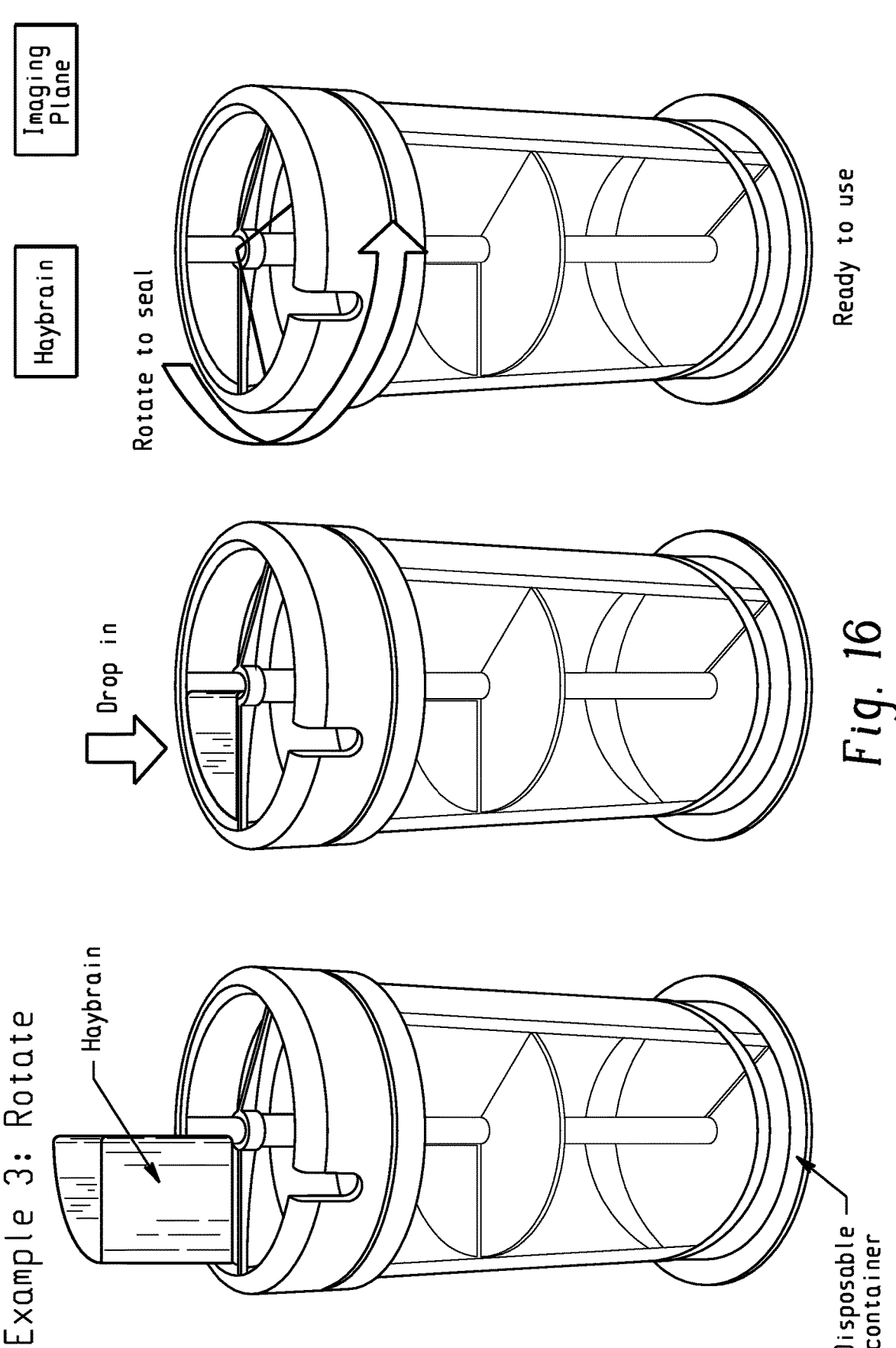
Figure 17:
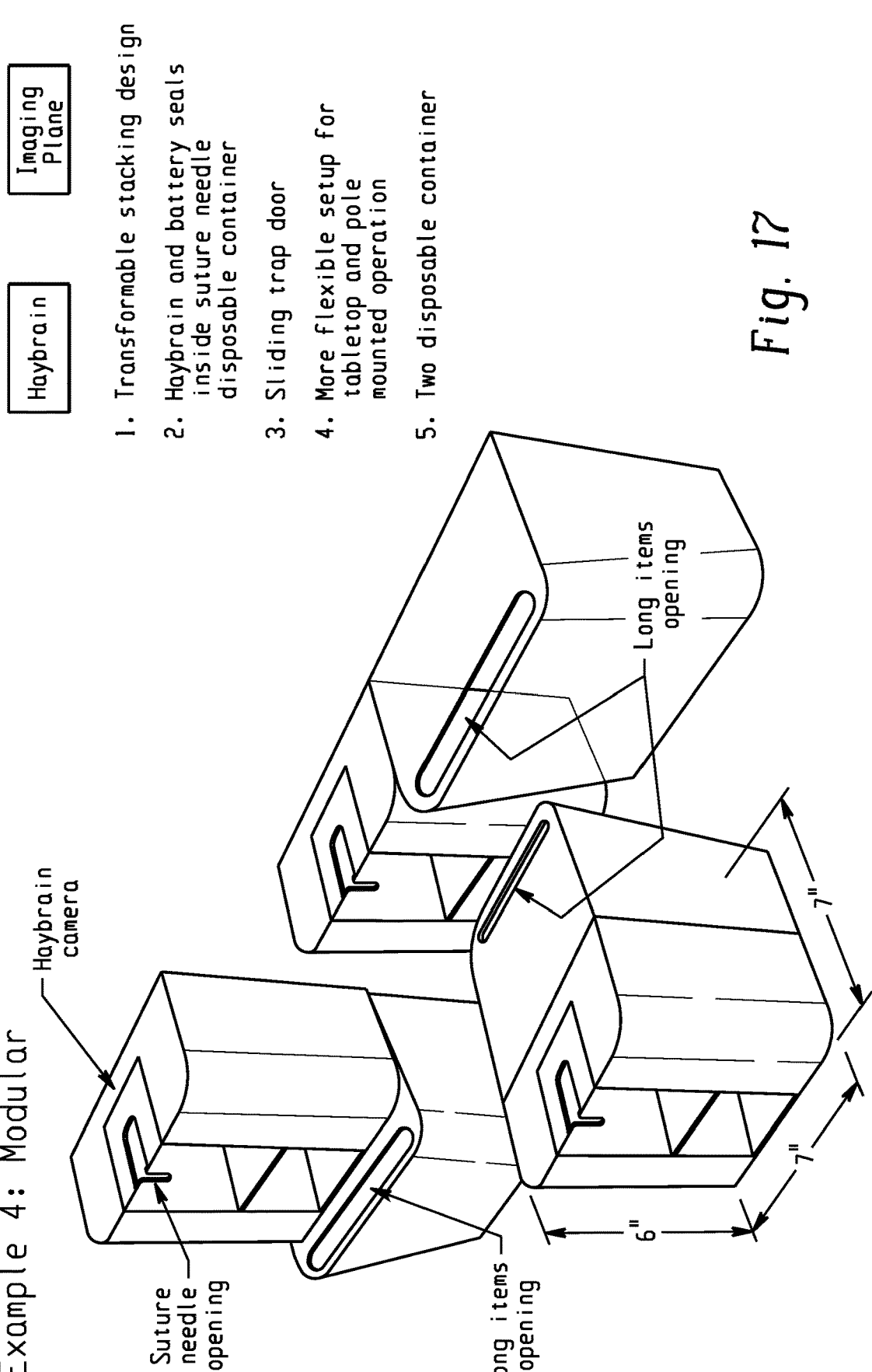
Figure 19:
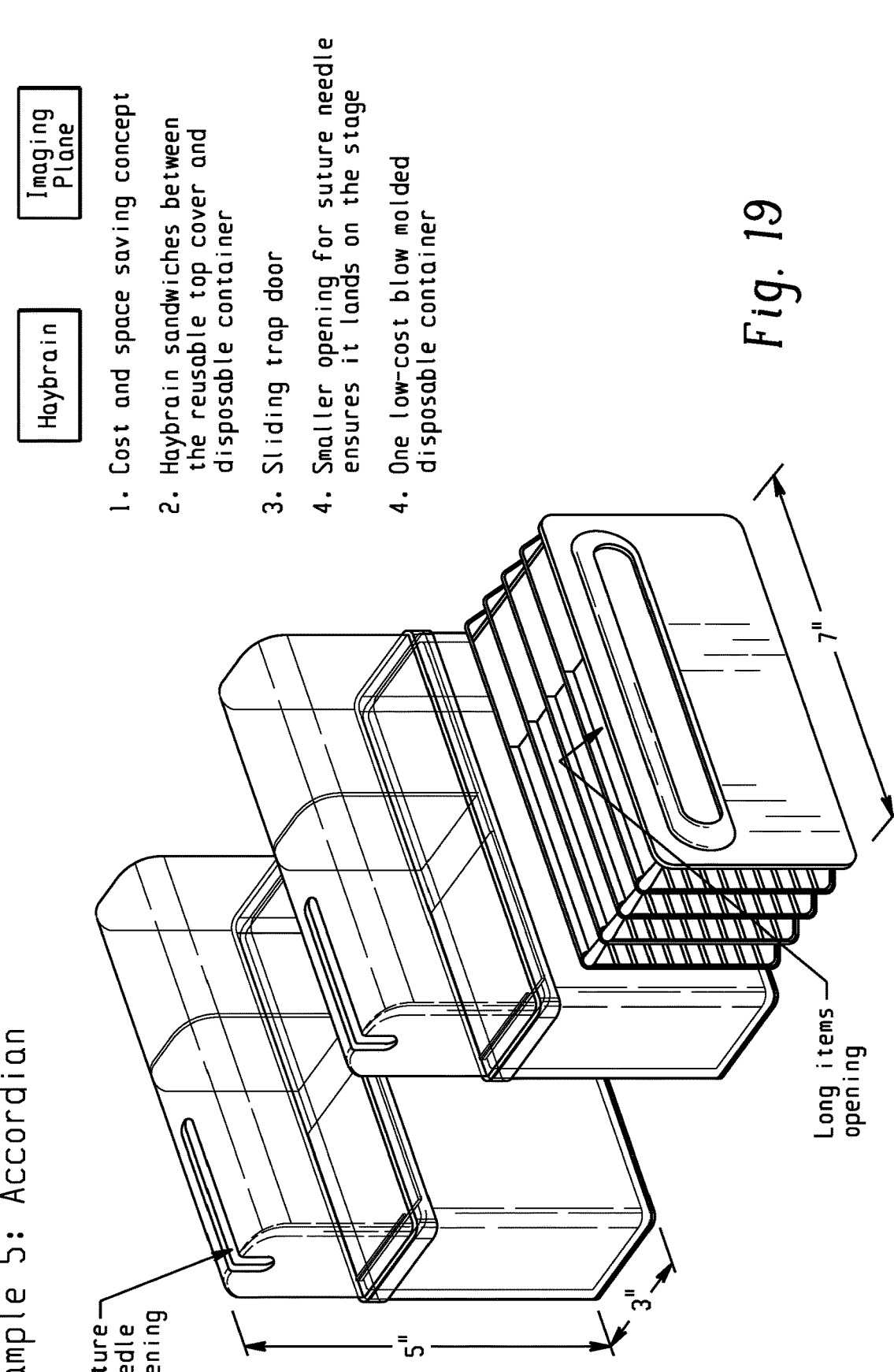

FIG. 9 depicts user interfaces for setting up an operating room procedure and initiating counting of needles in a pack. FIG. 10 depicts user interfaces for viewing the counts and for manually adjusting a count (e.g., accounting for x needles still present in a pack, where the remainder of the pack is being discarded into an appropriate container such as enclosure 1 without use of the automatic counting functionality of the apparatus 2). FIG. 11 depicts additional user interfaces in different orientations and arrangements, where per-enclosure counts are depicted for multiple enclosures used during the operation.

In embodiments, the counting apparatus 2 may include a suture thread cutting device at or near the point of needle deposit. FIG. 12 depicts example thread cutting devices that include a V shaped opening (bottom left) having a razor blade therein for cutting the suture thread such that a smaller portion (or no portion) remains connected to the needle when deposited (e.g., to improve needled-type detection via unobstructed images).

FIGS. 13-20 depict additional examples of counting apparatus shapes and physical arrangements. These figures illustrate example mechanisms for receiving the potentially non-sterile sensory equipment enclosure (Haybrain) and transitioning that non-sterile enclosure to an encapsulated position where it will not contaminate the surgery sterile field. The images also depict an imaging plane (highlighted in green, although the plane may be other colors including clear, white, and black). A camera position is also indicated by a "C" indicator.

Figure 21:
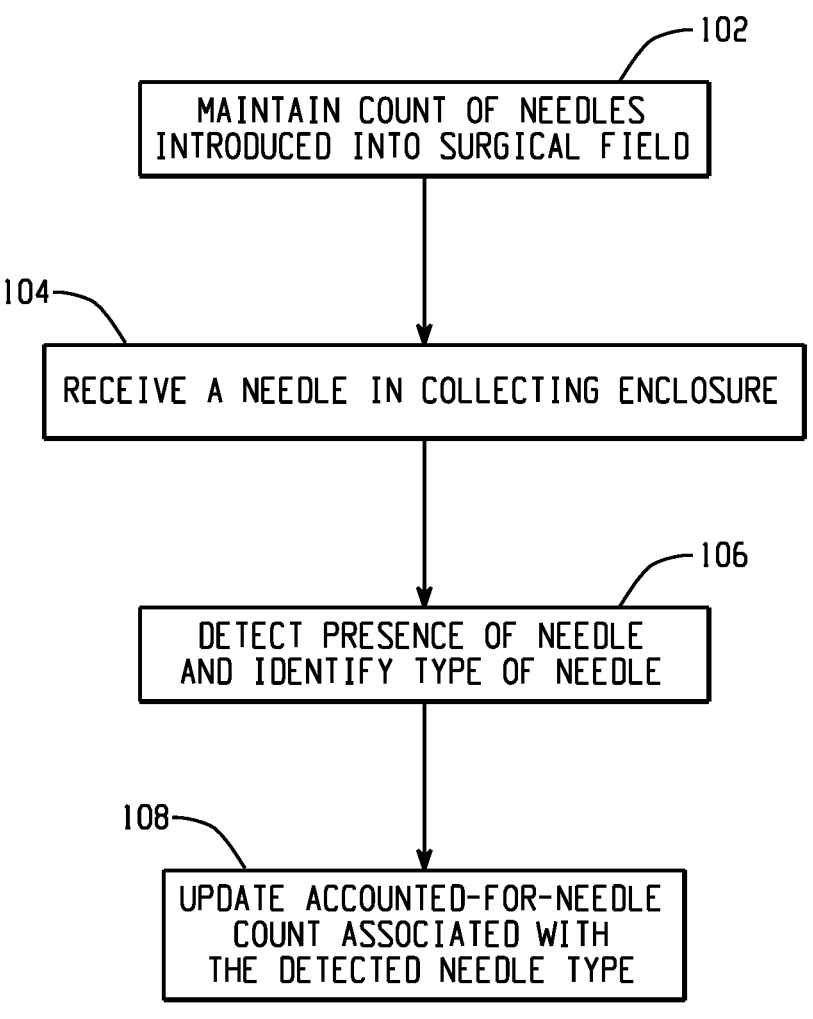
FIG. 21 is a flow diagram depicting a computer-implemented method of detecting a surgical needle in an operating room.

FIG. 21 is a flow diagram depicting a computer-implemented method of detecting a surgical needle in an operating room. At 102, a count of needles introduced into a surgical field associated with the operating room is maintained. At 104, a needle is received in a collecting enclosure. At 106, a sensor is used to detect the presence of the needle in the collecting enclosure and to identify a type associated with the needle. And at 108, an accounted-for-needle count associated with the detected needle type is updated based on said identifying As noted above, systems and methods as described herein may include a vision system that operates in conjunction with machine learning or artificial intelligence to detect and identify objects. In one embodiment, a visual detection methodology is used to determine that the item passing through the apparatus is an identifiable sharp and not another conductive material such as a water droplet. In one example, image recognition can determine the precise sharp or needle type as well. For example, inductive sensor detection may be utilized to detect the passing of the conductive material or sharps through a plane associated with the inductive sensor. That detection initiates capture of one or more images (e.g., high resolution images) of the passing material or an image of the inside of the container containing the sharps (e.g., needles) after it has passed. In other embodiments, other item detection mechanisms, or no initial item detection, may be used. By triggering the image capture of the object with the inductive sensor there may be benefits. For example, the number images to be analyzed are reduced to a smaller set for real-time processing compared to non-stop imaging. As another example, device power requirements may be reduced compared to continuous imaging. As another example, an amount computer processor and storage required may be reduced.

Images may be captured by a simple visible light camera system. A smart camera system may also be used that automatically adjusts lens focus, lighting, and provides software processing of images. Image processing may be performed on the device 2, improving speed and reliability, or off device where enhanced processing power may be utilized. High speed cameras may be used, especially in instances where the needle is imaged in motion, such as while falling through an imaging volume field of view (e.g., based on a trigger signal from an inductive sensor). Lighting in the field of view (e.g., polarization, shielding from outside light sources) may be provided to enhance image quality. Shuttering and strobing of light can improve image capture as well. Multi-frame bursts may also be beneficial for ensuring at least one quality image is captured. A reference point in the field of view may be utilized to promote focus. For example, microdots or other indicators of known size and other characterizations on a stage may be used to appropriately focus the camera. In an embodiment, captured images may be preprocessed (e.g., noise removal, contrast enhancing), segmented (e.g., threshold/region/gradient/classification based), and features may be extracted (e.g., needle length, width, area, perimeter, shape (size dependent or independent), color (e.g., mean and variance), and combinations thereof). In instances where needle type cannot be discerned for a particular need (e.g., due to debris), an image of the needle may be displayed on a screen in real time or later for identification and appropriate update of the counts. In an embodiment, the needle image is captured on a pre-marked surface having a mark (e.g., a unique mark) of known size and dimension. The mark allows for later determination of the location of the imaging (e.g., in which counting apparatus the image was taken). The known size and dimension further enables calibration for pixel counting or other image processing activities to enhance the ability to determine the size and shape of the needle being imaged relative to the mark of known size.

In examples, a deep learning algorithm such as YOLOv3 and Faster R-CNN can be pretrained on images and geometries captured (e.g., from CAD designs of the sharp manufacturers or images of sharps). The algorithm may use an intersection over union (IoU) method as well as by measuring the Euclidean distance between bounding box centroids. Deep learning-based object detection and tracking algorithms may be used in certain object detection methodologies in computer vision. Systems and methods as described herein may apply this to needle and sharp counting in surgical procedures. For example a 'Region-based Convolutional Neural Network' (R-CNN) may be used as an object detection methodology. In this method, the concept of region proposals and two-step detection are used. The method first generates a series of candidate bounding boxes and then performs classification and regression on these bounding boxes.

Single shot multi-box detect (SSD) may be used to discretize the output space into bounding boxes with different scales and aspect ratios, and conduct object detection using features from different levels of the neural network. 'You Only Look Once' (YOLO) is another method that may be utilized. Such a method performs object detection in real time with acceptable accuracy.

Faster R-CNN and YOLOv3 may be used alone or together for suture needle detection in terms of surgical sharp counting in an operating room procedure, ensuring the safe accounting for sharps used in a surgical procedure. Faster R-CNN utilizes CNNs for both region proposal and object detection. This configuration can significantly increase the computational efficiency. In one example, there are four components in Faster R-CNN: a feature extraction network, a region proposal network (RPN), region of interest (ROI) pooling layers, and detection layers. The feature extraction network in this study is a pretrained ResNet50. The ResNet50 consists of convolutional layers and skip connections. The convolutional layer is a commonly used layer in deep learning. Unlike fully connected layers in traditional neural networks, a convolutional layer uses a sliding window to scan through the image to do the convolution operations. The sliding window is like a regular filter except the weights of it are determined by the training of the neural network. Owing to the characteristics of the convolutional layer, it has been successfully applied to a variety of tasks in computer vision. The skip connections that connect two nonconsecutive layers may be used to resolve the training issue. The layer within a skip connection is called a residual block. These residual blocks can help the training of the deep neural network and can lead to better performance.

In certain systems and methods as described herein, either Faster R-CNN or YOLO-3 algorithms may be applied or both for extra confidence in the detection of a needle. Embodiments may include building of the image training from either the CAD data sources of the sharp manufacturers or by still images taken or both. Systems and methods can be configured to detect that the object was one of the sharps in the database and/or make a confidence judgement about the specific needle or sharp detected.

Note that in one embodiment the images were taken as the needle or sharp passes through the tube triggered by the inductive sensing of the falling object. In this embodiment there is no need to compare images to the previous images to find the new object as there should only be one sharp in the field of view. However, in another embodiment, the image may be taken inside the tray or enclosure, that captures all the used needles that have been previously captured. In this case it would be possible to determine if this new image contains an incremental needle that has been captured from the previous image and the coordinates or location of that additional needle.

In another embodiment, the sharps may be temporarily held and imaged individually so that the algorithms need only process one object at a time reducing computational time and resources needed to identify an object. In this embodiment a machine vision blob detection tool would identify the edges of the sharp in the image. With the edges defined by the blob tool, software can assess the dimensions of the object in the image and using an algorithm identify it based on how the algorithm was trained. The sharp may be temporarily held using a variety of mechanisms such as: a magnetic stage to help force orientation; air pressure/ vacuum; diaphragm shutter; pivoting stage; vibratory stage—to help coerce orientation. Other modalities could utilize laser scanning to identify the sharp. The presence of an item (e.g., a sharp) at a point in a system may be detected using a mechanism such as: measuring a disturbance in a magnetic field. (inductive); a light curtain; a mechanical trigger; voice activation; a BGA Grid.

When imaging a needle, mechanisms may be utilized to help ensure that the needle is in a proper orientation for imaging (e.g., not stuck on its side due to a still-connected suture end, fluids, or other debris). In one example, a magnet under an imaging stage is energized upon detection of a needle entering the stage area (e.g., via an inductive sensor). Once one or more images of the needle is captured, the magnet is deenergized to allow the needle to be dumped, wiped, or otherwise moved to the permanent storage of the enclosure. In examples, tape or adhesive may be used to promote proper orientation. In embodiments, a continuous strip of tape may be pulled through the imaging region over time. In one example, the stage is configured to vibrate to lay flat. In another example, a transparent surface is positioned on top of the stage (e.g., via a hinge forming a Venus-fly-trap arrangement).

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

A variety of different sensors may be utilized as part of a counting apparatus. Those sensors may be configured to detect the presence of needles or other objects in a collecting enclosure. Further, the sensors may be configured to provide data for identifying characteristics of those needles or other objects, such as size (e.g., a 5 mm needle, a 30 mm needle), shape (e.g., a chord length, a diameter), a needle/object material, and a needle/object type. In embodiments, the sensor may be configured to detect and provide characteristic data even when a needle/object is coated with blood or moisture from the patient or operating environment. Example sensors include a micro balance configured to detect a weight change. Such a system may need to be calibrated to account for differences from base needle weights caused by debris (e.g. blood moisture passing entering the collecting enclosure), which could result in false positives or detection of multiple needles when only one is received. In embodiments, an optical detector may be utilized to detect the presence of an object. In such embodiments, the optical detector may take the form of a vision system that is configured to determine type and characteristics of objects, such as through machine learning using training images. In embodiments, inductive sensors may be utilized, such as ring sensors and vertical tube sensors. In embodiments, the sensitivity of those sensors are tuned and orientation of objects is controlled (e.g., as it falls into a collecting enclosure to avoid errors (e.g., undetected needles that traverse the inductive sensor flat relative to the inductive sensor plane. For example, a funnel may be used to direct a needle through the inductive sensor in a desired orientation. In instances where multiple inductive sensors are utilized to avoid missing needles, software algorithms are implemented to avoid double counting single detected needles (e.g., algorithms that avoid counting more than 1 needle within a threshold period of time). In embodiments, an accelerometer is implemented to ensure the a funnel angle is correct so as to discourage needles from going straight through the center of the funnel without contact, but to also discourage needles from getting stuck in the funnel without traversing to the collecting enclosure. In embodiments, the funnel includes a hydrophobic coating on its inside to prevent needles from becoming lodged inside of the funnel.

In one example, an intra-operative apparatus and system are positioned within the aseptic surgical area related to surgical needles. Surgical needle detection and counting methods are provided. Aspects of the apparatus include a sensor device for detecting the presence of surgical needles; an automated surgical needle counting system configured to tabulate individual detection events; and a method to calculate variance from intra-operative surgical needle count data. The system, methods and apparatus may include features such as an inductive sensor, capacitive sensor, photoelectric sensor, through-beam sensor, retroreflective sensor, infrared sensor, electromagnetic sensor, acoustic wave sensor (e.g., a guitar pickup), a visible light sensor, a light eclipse sensor, a pressure sensor, detected short circuits across an XY ball grid array on which a needle is placed, and an ultrasonic sensor adapted to detect entry and exit of a surgical needle identifier associated with each of a plurality of suture needles.

In an example, an Electronic Article Surveillance (EAS) scanner may be included that is adapted to detect the presence of a surgical needle having an EAS identifier associated with each of the plurality of surgical needles. A control circuit may be configured to determine and provide an indication that all the suture needles have been accounted for, or that one or more surgical needles still remain in the sterile filed. Systems of the invention may further include additional components, such as surgical needle identification and tracking devices. Systems of the invention find use in a variety of methods and applications, including tracking of surgical needles during a surgical procedure.

In an example, an apparatus system and associated methods are disclosed for protecting operating room personnel from the sharp ends of contaminated suture needles following surgical use on a patient. Systems and methods relate to a design for safe intraoperative and post-operative handling of contaminated suture needles. An apparatus is composed of a sterile disposable receptacle that can expand and collapse that has a self-sealing interface and cover for temporary attachment to a contaminated suture needle detection and counting device. The receptacle may be a sterile circular puncture-resistant asymmetric paraboloid comprised of a malleable rubber cover and flexible plastic side walls and bottom. The receptacle may be expanded and secured onto the contaminated suture needle detection and counting device forming a closed system. The receptacle may provide a self-sealing perforation in the cover it receives the contaminated suture needles. When the receptacle is full, the entire receptacle is removed from the suture needle detection and counting device and the receptacle collapsed. The receptacle may be designed to irreversibly seal permanently enclosing the suture needle and will not permit suture needle to puncture or come out of the receptacle. The entire receptacle may be discarded in a medical waste container. The collapsible mechanism may include a plurality of discrete sections movable relative to one another to move the expandable portion between a collapsed configuration and an expanded configuration.

It is claimed:

1. A surgical needle counting device for an operating room, comprising:
   a collecting enclosure;

a counting apparatus having a sensor configured for determining when a needle is dropped into the collecting enclosure;
   the counting apparatus being configured to maintain a first count of needles introduced into a surgical field associated with the operating room and a second count of needles accounted for in the counting apparatus;
   wherein the second count of needles is associated with the collecting enclosure.

2. The device of claim 1, wherein the counting apparatus comprises a vision system trained to identify needles by type based on training images depicting different, pre-identified needle types.

3. The device of claim 1, wherein the counting apparatus is configured to increase the second count of needles and to emit a visible or audio signal upon determining that the needle has been dropped into the collecting enclosure.

4. The device of claim 1, wherein the second count of needles is transmitted to a mobile device in the operating room for display.

5. The device of claim 1, wherein the second count of needles is transmitted to a remote database for auditing of an operating room procedure.

6. The device of claim 1,
   wherein the collecting enclosure is removable from the device;
   wherein the counting apparatus is configured to detect attachment of a new removable collecting enclosure, wherein a new count of needles is stated based on said detecting attachment of the new removable collecting enclosure.

7. The device of claim 1,
   wherein the counting apparatus is configured to further maintain a total count of needles accounted for associated with an operating room procedure that spans multiple collecting enclosures.

8. The device of claim 1, wherein the counting apparatus is configured to issue an alert when the second count of needles reaches a threshold indicating that the collecting enclosure is full.

9. The device of claim 1, wherein the counting apparatus is configured to track counts of different types of needles introduced into the surgical field.

10. The device of claim 1, wherein the sensor is configured to discern a needle type when the needle is dropped into the collecting enclosure.

11. The device of claim 1, wherein the sensor is an infrared sensor, an electromagnetic sensor, an acoustic wave sensor, a visible light sensor, or a pressure sensor.

12. The device of claim 1, wherein the collecting enclosure includes a magnet for retaining a deposited needle at a desired location.

13. The device of claim 12, wherein the magnet is configured to hold a deposited needle at a sensing position in the collecting enclosure where a needle type is detected by the sensor;
   wherein the collecting enclosure is configured to allow the deposited needle to leave the sensing position following said needle type detecting.

14. The device of claim 13, wherein a visual image is made available on a display device for manual counting of needles in the collecting enclosure via physical touch of the image on the display device and an incremental counter.

15. The device of claim 1, further comprising a camera configured for viewing inside the collecting enclosure and capturing an image to validate the second count of needles.

16. The device of claim 15, further comprising image recognition software configured to identify a count of needles present in the image for comparison with the second count of needles.

17. The device of claim 1, wherein the collecting enclosure is collapsible, expandable, and self-sealing.

18. The device of claim 1, wherein the counting apparatus includes multiple sensors and software configured to prevent double counting of needles dropped into the collecting enclosure and sensed by more than one of the multiple sensors.

19. The device of claim 1, further comprising an intake funnel coated with a hydrophobic material configured to transit a deposited needle into the collecting enclosure.

20. The device of claim 1, wherein the counting apparatus comprises a vision system trained via machine learning, the vision system being configured to capture a color, a size, and a shape of succor, wherein the vision system is configured to identify both a succor and a needle type associated with the needle.

21. The device of claim 1, wherein the second count is associated with a unique identifier associated with the collecting enclosure.

22. The device of claim 21, wherein the collecting enclosure is configured to be removed and replaced with a new collecting enclosure;

wherein the new collecting enclosure is associated with a second unique identifier and a third count of needles.

23. The device of claim 22, further comprising a surgical needle management software application configured to track unique counts of needles associated with each of a plurality of collecting enclosures.

24. A method of detecting a surgical needle in an operating room, comprising:

maintaining a first count of needles introduced into a surgical field associated with the operating room;

receiving a needle in a collecting enclosure;

using a sensor to detect the presence of the needle in the collecting enclosure and to identify a type associated with the needle;

updating an second accounted-for-needle count associated with the detected needle type and the collecting enclosure based on said identifying.

\* \* \* \* \*